United States Patent
Khosrow-Khavar et al.

(10) Patent No.: US 11,504,047 B2
(45) Date of Patent: Nov. 22, 2022

(54) SENSOR APPARATUSES, METHODS OF OPERATING SAME, AND SYSTEMS INCLUDING SAME, AND METHODS AND SYSTEMS FOR SENSING AND ANALYZING ELECTROMECHANICAL CHARACTERISTICS OF A HEART

(71) Applicant: HEART FORCE MEDICAL INC., Vancouver (CA)

(72) Inventors: Farzad Khosrow-Khavar, North Vancouver (CA); Kay Jessel, West Vancouver (CA); Sean Ross, North Vancouver (CA)

(73) Assignee: Heart Force Medical Inc., Vancouver (CA)

( * ) Notice: Subject to any disclaimer, the term of this patent is extended or adjusted under 35 U.S.C. 154(b) by 170 days.

(21) Appl. No.: 16/958,689

(22) PCT Filed: Dec. 3, 2018

(86) PCT No.: PCT/CA2018/051542
§ 371 (c)(1),
(2) Date: Jun. 27, 2020

(87) PCT Pub. No.: WO2019/126866
PCT Pub. Date: Jul. 4, 2019

(65) Prior Publication Data
US 2020/0405170 A1 Dec. 31, 2020

Related U.S. Application Data

(60) Provisional application No. 62/658,478, filed on Apr. 16, 2018, provisional application No. 62/611,462, filed on Dec. 28, 2017.

(51) Int. Cl.
*A61B 5/349* (2021.01)
*A61B 5/0205* (2006.01)
(Continued)

(52) U.S. Cl.
CPC ............ *A61B 5/349* (2021.01); *A61B 5/0205* (2013.01); *A61B 5/1102* (2013.01); *G16H 50/30* (2018.01);
(Continued)

(58) Field of Classification Search
CPC ..... A61B 5/349; A61B 5/0205; A61B 5/1102; A61B 5/021; A61B 5/14551; G16H 50/50; G16H 50/30
See application file for complete search history.

(56) References Cited

U.S. PATENT DOCUMENTS

| 4,905,706 A | 3/1990 | Duff et al. |
| 5,036,857 A | 8/1991 | Semmlow et al. |

(Continued)

FOREIGN PATENT DOCUMENTS

| EP | 3135194 A1 | 3/2017 |
| WO | 2013121431 A1 | 8/2013 |

(Continued)

OTHER PUBLICATIONS

Extended European Search Report in EP18896426.6, dated Sep. 3, 2021.

(Continued)

*Primary Examiner* — Carl H Layno
*Assistant Examiner* — Aya Ziad Bakkar
(74) *Attorney, Agent, or Firm* — Polsinelli PC

(57) ABSTRACT

Sensor apparatuses, methods of operating the sensor apparatuses, and systems including the sensor apparatuses are disclosed. Methods of analyzing electromechanical characteristics of a heart are also disclosed.

26 Claims, 18 Drawing Sheets

(51) Int. Cl.
  *A61B 5/11*   (2006.01)
  *A61B 5/021*  (2006.01)
  *G16H 50/50*  (2018.01)
  *G16H 50/30*  (2018.01)
  *A61B 5/1455* (2006.01)

(52) U.S. Cl.
  CPC .............. *G16H 50/50* (2018.01); *A61B 5/021* (2013.01); *A61B 5/14551* (2013.01)

(56) References Cited

U.S. PATENT DOCUMENTS

| | | | |
|---|---|---|---|
| 6,048,319 | A | 4/2000 | Hudgins et al. |
| 7,922,669 | B2 | 4/2011 | Zhang et al. |
| 8,700,137 | B2 | 4/2014 | Albert |
| 9,451,921 | B2 | 9/2016 | Schmidt et al. |
| 2007/0032749 | A1 | 2/2007 | Overall et al. |
| 2007/0225614 | A1 | 9/2007 | Naghavi et al. |
| 2011/0066041 | A1 | 3/2011 | Pandia et al. |
| 2013/0066168 | A1 | 3/2013 | Yang et al. |
| 2014/0221859 | A1 | 8/2014 | Albert |
| 2014/0276119 | A1 | 9/2014 | Venkatraman et al. |
| 2015/0025335 | A1* | 1/2015 | Jain ..................... A61B 5/1102 600/509 |
| 2015/0038856 | A1 | 2/2015 | Houlton et al. |
| 2015/0133806 | A1 | 5/2015 | Airaksinen et al. |
| 2015/0305687 | A1 | 10/2015 | Schmidt et al. |
| 2016/0135717 | A1 | 5/2016 | Koivisto et al. |
| 2016/0220152 | A1* | 8/2016 | Meriheinä ............ A61B 5/7246 |
| 2016/0345844 | A1 | 12/2016 | McCombie et al. |
| 2016/0361041 | A1 | 12/2016 | Barsimantov et al. |
| 2018/0092533 | A1 | 4/2018 | Yee et al. |
| 2018/0192888 | A1 | 7/2018 | Yee et al. |
| 2018/0214030 | A1 | 8/2018 | Migeotte et al. |
| 2018/0303382 | A1 | 10/2018 | Airaksinen et al. |

FOREIGN PATENT DOCUMENTS

| | | | |
|---|---|---|---|
| WO | 2017036887 | A1 | 3/2017 |
| WO | 2017060569 | A1 | 4/2017 |
| WO | 2017174814 | A1 | 10/2017 |

OTHER PUBLICATIONS

International Search Report in PCT/CA2018/051542, dated Jan. 10, 2019.
Written Opinion of the International Searching Authority in PCT/CA2018/051542, dated Jan. 10, 2019.
Dehkordi et al., "Monitoring Torso Acceleration for Estimating Respiratory Flow and Efforts for Sleep Apnea Detection", IEEE EMBS, pp. 6345-6348, Aug. 28-Sep. 1, 2012.
Khosrow-khavar et al., "A New Seismocardiography Segmentation Algorithm for Diastolic Timed Vibrations", IEEE EMBS, pp. 7278-7281, 2013.
Khosrow-khavar et al., "Automatic and Robust Delineation of the Fiducial Points of the Seismocardiogram Signal for Noninvasive Estimation of Cardiac Time Intervals", IEEE Transactions on Biomedical Engineering, vol. 64, No. 8, pp. 1701-1710, Oct. 2016.
Khosrow-khavar et al., "Automatic Annotation of Seismocardiogram with Higher Frequency Precordial Accelerations", IEEE Journal of Biomedical and Health Informatics, vol. 19, No. 4, pp. 1428-1434, Jul. 2015.
Khosrow-khavar et al., "Moving Toward Automatic and Standalone Delineation of Seismocardiogram Signal", Annual International Conference of the IEEE Engineering in Medicine and Biology Society, pp. 7163-7716, 2015.
Khosrow-khavar et al., "Moving Toward Automatic and Standalone Delineation of Seismocardiogram Signal", IEEE EMBC2015 Milan, Italy, Aug. 2015.
Laurin et al., "Accurate and consistent automatic seismocardiogram annotation without concurrent ECG", Physiological Measurement, vol. 37, pp. 1588-1604, 2016.
Laurin et al., "Seismocardiograms Return Valid Heart Rate Variability Indices", Computing in Cardiology, vol. 40, pp. 413-416, 2013.
Ngai et al., "Comparative Analysis of Seismocardiogram Waves with the Ultra-Low Frequency Ballistocardiogram", IEEE EMBS, pp. 2851-2854, Sep. 2009.
Sahoo et al., "A Cardiac Early Warning System with Multi Channel SCG and ECG Monitoring for Mobile Health", Sensors 2017 [online], vol. 17, No. 4, pp. 1-28, Mar. 29, 2017, retrieved from https://www.mdpi.com/1424-8220/17/4/711.
Salerno et al., "Exercise Seismocardiography for Detection of Coronary Artery Disease", American Journal of Noninvasive Cardiology, vol. 6, pp. 321-330, 1992.
Tadi et al., "Gyrocardiography: A New Non-invasive Monitoring Method for the Assessment of Cardiac Mechanics and the Estimation of Hemodynamic Variables", Scientific Reports, vol. 7, pp. 1-11, Jul. 28, 2017, retrieved from https://www.nature.com/articles/s41598-017-07248-y.
Tavakolian et al., "Analysis of Seismocardiogram Capability for Prediction of Mild to Moderate Haemorrhage; Preliminary Results", Computing in Cardiology, vol. 40, pp. 1107-1109, 2013.
Tavakolian et al., "Analysis of Seismocardiogram Capability for Trending Stroke Volume Changes: A Lower Body Negative Pressure Study", Computing in Cardiology, vol. 39, pp. 733-736, 2012.
Tavakolian et al., "Comparative Analysis of Infrasonic Cardiac Signals", Computers in Cardiology, vol. 36, pp. 757-760, 2009.
Tavakolian et al., "Estimating Cardiac Stroke Volume from the Seismocardiogram Signal", Canadian Medical and Biological Engineering Society Proceedings, vol. 33, No. 1, Jun. 2010.
Tavakolian et al., "Estimation of Hemodynamic Parameters from Seismocardiogram", Computing in Cardiology, vol. 37, pp. 1055-1058, 2010.
Tavakolian et al., "Estimation of Hemodynamic Parameters from Seismocardiogram", Conference Paper, Oct. 2010.
Tavakolian et al., "Improvement of ballistocardiogram processing by inclusion of respiration information", Journal of Physiological Measurement, vol. 29, pp. 771-781, 2008.
Tavakolian et al., "Infrasonic Cardiac Signals: Complementary Windows to Cardiovascular Dynamics", IEEE EMBS, pp. 4275-4278, Aug. 30-Sep. 3, 2011.
Tavakolian et al., "Myocardial Contractility: A Seismocardiography Approach", IEEE EMBS, pp. 3801-3804, Aug. 28-Sep. 1, 2012.
Tavakolian et al., "Precordial vibrations provide noninvasive detection of early-stage hemorrhage", Journal of Shock, vol. 41, No. 2, pp. 91-96, Feb. 2014.
Tavakolian et al., "Respiration Analysis of the Sternal Ballistocardiograph Signal", Computers in Cardiology, vol. 35, pp. 401-404, 2008.
Tavakolian et al., "Seismocardiographic Adjustment of Diastolic Timed Vibrations", IEEE EMBS, pp. 3797-3800, 2012.
Tavakolian, "Systolic Time Intervals and New Measurement Methods", Cardiovascular Engineering and Technology, vol. 7, No. 2, pp. 118-125, 2016.
Verma et al., "Preliminary Results for Estimating Pulse Transit Time Using Seismocardiogram", Journal of Medical Devices, vol. 9, Jun. 2015.
Verma et al., "Pulse Transit Time Extraction from Seismocardiogram and its Relationship with Pulse Pressure", Computing in Cardiology, vol. 42, pp. 37-40, 2015.
Wilson et al., "Diagnostic Accuracy of Seismocardiography Compared with Electrocardiography for the Anatomic and Physiologic Diagnosis of Coronary Artery Disease During Exercise Testing", American Journal of Cardiology, vol. 71, pp. 536-545, 1993.

* cited by examiner

SENSOR APPARATUSES, METHODS OF OPERATING SAME, AND SYSTEMS INCLUDING SAME, AND METHODS AND SYSTEMS FOR SENSING AND ANALYZING ELECTROMECHANICAL CHARACTERISTICS OF A HEART

FIELD

This disclosure relates generally to sensor apparatuses, to methods of operating the sensor apparatuses, and to systems including the sensor apparatuses. This disclosure also relates generally to methods and systems for sensing and analyzing electromechanical characteristics of a heart of a subject.

RELATED ART

Heart disease is a major cause of death in humans. In many cases, heart conditions may be treated following early detection. However, known systems may not identify heart conditions conveniently or accurately, which can lead to preventable death from heart disease.

SUMMARY

According to one embodiment, there is provided a method of operating a sensor apparatus, the method comprising: causing the sensor apparatus to measure at least one measurement of at least one characteristic of a heart of a subject during a period of time; and causing the sensor apparatus to measure a force by which the sensor apparatus is held against the subject.

According to another embodiment, there is provided a method of operating a sensor apparatus, the method comprising: causing the sensor apparatus to measure a time series of ECG measurements during a first period of time by at least one capacitive sensor on the sensor apparatus when the at least one capacitive sensor is positioned to measure ECG voltages of a subject; causing the sensor apparatus to measure a time series of measurements of movement caused by a heart of the subject during a second period of time at least overlapping with the first period of time; and causing at least one signal interface to produce at least one output signal responsive to the time series of ECG measurements and to the time series of measurements of movement.

According to another embodiment, there is provided a sensor system comprising: a sensor apparatus comprising a means for measuring at least one measurement of at least one characteristic of a heart of a subject during a period of time; and a means for measuring a force by which the sensor apparatus is held against the subject.

According to another embodiment, there is provided a sensor system comprising a sensor apparatus comprising: a means for measuring a time series of ECG measurements during a first period of time by at least one capacitive sensor on the sensor apparatus when the at least one capacitive sensor is positioned to measure ECG voltages of a subject; and a means for measuring a time series of measurements of movement caused by a heart of the subject during a second period of time at least overlapping with the first period of time.

According to another embodiment, there is provided a sensor system comprising a sensor apparatus comprising: at least one heart characteristic sensor operable to measure at least one characteristic of a heart of a subject during a period of time; and a force sensor operable to measure a force by which the sensor apparatus is held against the subject.

According to another embodiment, there is provided a sensor system comprising a sensor apparatus comprising: an ECG sensor comprising a capacitive sensor; and at least one movement sensor.

According to another embodiment, there is provided a method of analyzing electromechanical characteristics of a heart, the method comprising producing at least one inference, wherein producing the at least one inference comprises analyzing, in a plurality of models associated with respective different types of inference, at least: a time series of ECG measurements of the heart and measured during a first period of time; and a time series of measurements of movement caused by a heart of the subject during a second period of time at least overlapping with the first period of time.

According to another embodiment, there is provided a method of analyzing electromechanical characteristics of a heart, the method comprising producing at least one inference in response to, at least, a time series of ECG measurements of the heart and measured during a first period of time, wherein producing the at least one inference comprises feature extraction of at least one time segment of, at least, a time series of measurements of movement caused by a heart of the subject during a second period of time at least overlapping with the first period of time.

According to another embodiment, there is provided at least one computer-readable medium comprising codes stored thereon that, when executed by at least one processor, cause the at least one processor to implement any one of the methods.

According to another embodiment, there is provided at least one computing device programmed to implement any one of the methods.

Other aspects and features will become apparent to those ordinarily skilled in the art upon review of the following description of illustrative embodiments in conjunction with the accompanying figures.

DETAILED DESCRIPTION

A. Sensor Systems

Figure 1:
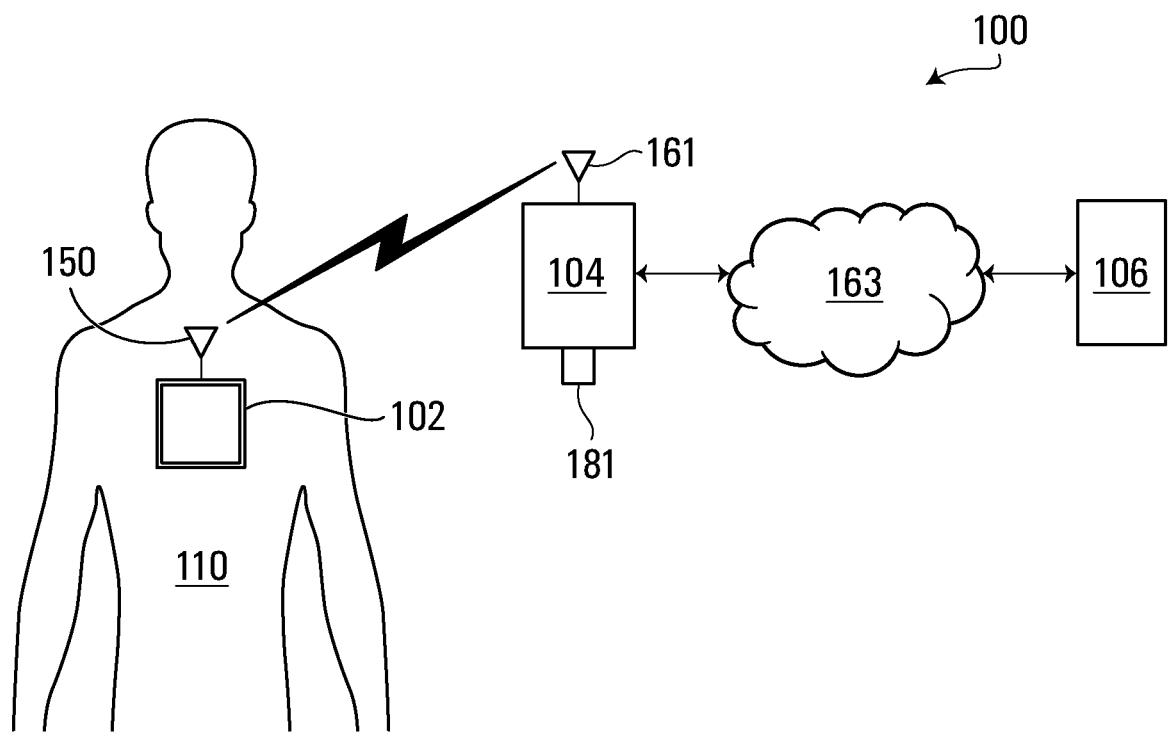
FIG. 1 illustrates a sensor system according to one embodiment.

Referring to FIG. 1, a sensor system according to one embodiment is shown generally at 100 and includes a sensor apparatus 102, a local computing device 104 separate from the sensor apparatus 102, and a remote computing device 106 separate from the sensor apparatus 102 and from the local computing device 104. The local computing device 104 may, for example, be a laptop computer, a personal computer, a tablet computer, a smartphone, a smartwatch, or another computing device. The remote computing device 106 may, for example, be a personal computer, a server computer, or another computing device, and the remote computing device 106 may include one or more computing devices, which may function as cloud computing devices, for example.

Figure 2:
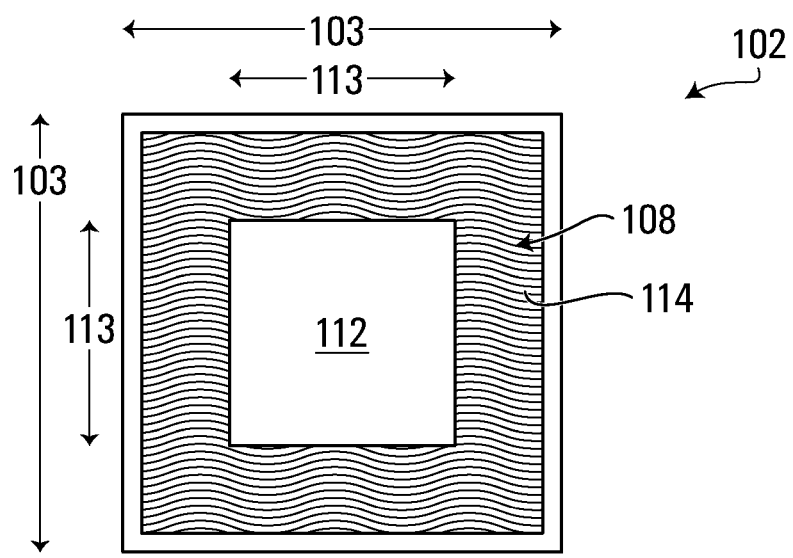
FIG. 2 is an end view of a sensor apparatus of the sensor system of FIG. 1.
Figure 3:
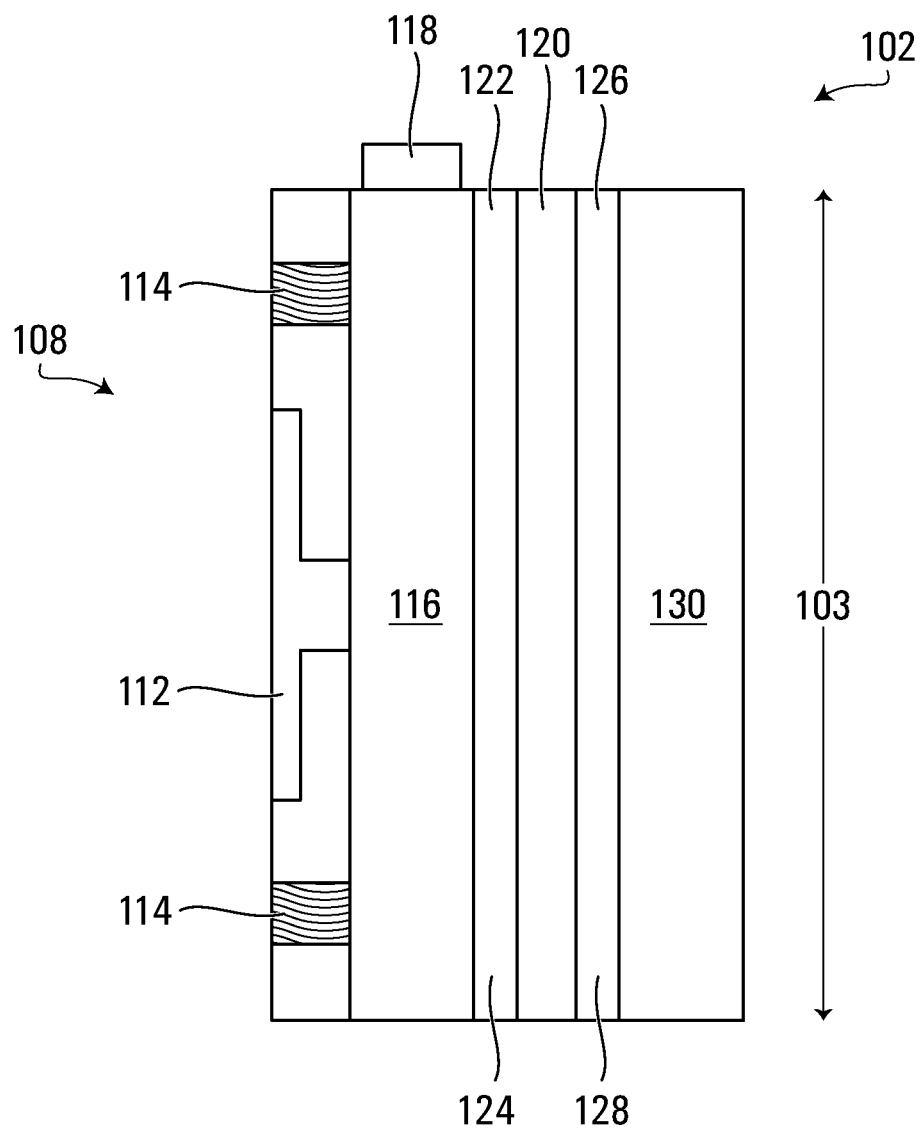
FIG. 3 is a side view of the sensor apparatus of FIG. 2.

Referring to FIGS. 1, 2, and 3, the sensor apparatus 102 in the embodiment shown has a generally square shape having side lengths 103 of approximately 3 centimeters ("cm"). However, alternative embodiments may have different shapes and may be of different sizes.

The sensor apparatus 102 in the embodiment shown has a sensor side shown generally at 108 and positionable against a subject 110, which may be a human subject for example. The sensor apparatus 102 includes a capacitive sensor 112 (such as an insulated copper-fill capacitive electrode, for example) exposed on the sensor side 108 so that, when the sensor side 108 is positioned against the subject 110 as shown in FIG. 1, the capacitive sensor 112 may be positioned to measure electrocardiogram ("ECG") voltages of the subject 110. The capacitive sensor 112 may thus function as an ECG sensor or as an electrocardiogram ("ECG").

In the embodiment shown, the capacitive sensor 112 may not need to be attached to the subject 110, so the capacitive sensor 112 may also be referred to as a "capacitive contactless sensor" or more generally as a "contactless sensor". Further, although some ECG sensors may require three or more leads to be adhered to a subject, the capacitive sensor 112 may, in some embodiments, be a single lead that, together with the rest of the sensor apparatus 102, may be held against a subject rather than being adhered to the subject. In some embodiments, such a sensor apparatus including such a single lead that may be held against a subject may be more attractive to some users, such as consumers who may prefer a sensor system that may be easier to use than other ECG sensors.

Also, in the embodiment shown, the capacitive sensor 112 has a generally square shape having side lengths 113 of approximately 1.5 cm. However, alternative embodiments may differ. For example, sensor apparatuses according to other embodiments may include alternatives to the capacitive sensor 112, such as one or more ECG sensors that may not necessarily be capacitive sensors, and that may have other shapes, such as a circular shape for example. However, in some embodiments, the surface area may be the same (namely 1.5 cm×1.5 cm=2.25 cm$^2$, approximately) or similar even for different shapes of an ECG sensor. In other embodiments, an alternative to the capacitive sensor 112 may include two, three, or more than three leads. Further, some embodiments may omit an ECG sensor.

The sensor apparatus 102 also includes a force sensor such as a force-sensing resistor 114 having a resistance that varies according to a force by which the sensor side 108 of the sensor apparatus 102 is held against the subject 110. The sensor apparatus 102 also includes an amplifier 116 that amplifies ECG measurements from the capacitive sensor 112. However, alternative embodiments may differ. For example, alternative sensor apparatuses may include alternatives to the force-sensing resistor 114, such as one or more force sensors that may not necessarily be force-sensing resistors. As another example, alternative sensor apparatuses may include alternative circuitry, such as more or fewer amplifiers for example.

Referring now to FIG. 3, the sensor apparatus 102 also includes a pulse oximeter 118 that may measure pulse rate and/or oxygen saturation in blood of the subject 110. However, alternative embodiments may differ. For example, some embodiments may omit the pulse oximeter 118, and some embodiments may include one or more alternatives to the pulse oximeter 118.

The sensor apparatus 102 also includes a movement isolation layer 120, at least one movement sensor 122 in a layer 124 on the sensor side 108 of the movement isolation layer 120, and at least one reference movement sensor 126 in a layer 128 on a side of the movement isolation layer 120 opposite the layer 122. Therefore, when the sensor side 108 of the sensor apparatus 102 is positioned against the subject 110 near a heart of the subject 110, the at least one movement sensor 122 may move in response to movement caused by the heart of the subject 110, and the at least one movement sensor 122 may measure movement caused by the heart of the subject 110. The movement isolation layer 120 may isolate the at least one reference movement sensor 126 from such movement caused by the heart of the subject 110, so that the at least one reference movement sensor 126 may measure body movement of the subject 110, such as rotation or locomotion of the subject 110 for example, so that a difference between movement measured by the at least one movement sensor 122 and movement measured by the at least one reference movement sensor 126 may represent an accurate measurement of movement caused by the heart of the subject 110. In some embodiments, the at least one movement sensor 122 may be more sensitive than the at least one reference movement sensor 126.

In various different embodiments, the at least one movement sensor 122 and the at least one reference movement sensor 126 may include different movement sensors, such as one or more internal or external single-axis, double-axis, or multi-axis accelerometers, gyroscopes, other sensors, or combinations of more than one thereof. As a result, the at least one movement sensor 122 and the at least one reference movement sensor 126 may measure linear acceleration (or, more generally, linear movement) caused by a heart (and thus may function as a seismocardiogram ("SCG")) and/or may measure rotational (or angular) velocity (or, more generally, rotational movement) caused by a heart (and thus may function as a gyrocardiogram ("GCG")). In some embodiments, such measured linear acceleration (or linear movement) may be in, at least, a linear direction towards and away from the subject, which may be referred to as a "z" direction. In other embodiments, such measured linear acceleration (or linear movement) may be in two linear directions. In other embodiments, such measured linear acceleration (or linear movement) may be in three linear directions. In some embodiments, such measured rotational velocity (or rotational movement) may be around at least one axis of rotation. In other embodiments, such measured rotational velocity (or rotational movement) may be around two axes of rotation. In other embodiments, such measured rotational velocity (or rotational movement) may be around three axes of rotation.

Therefore, in general, movement sensors as described herein may measure linear movement (such as linear acceleration, for example) in one, two, or three linear directions, may measure rotational movement (such as rotational velocity, for example) around one, two, or three axes of rotation, or may measure any combination thereof. Further, in general, measurements of movement as described herein may be measurements of linear movement (such as linear acceleration, for example) in one, two, or three linear directions, may be measurements of rotational movement (such as rotational velocity, for example) around one, two, or three axes of rotation, or may be measurements of any combination thereof.

In some embodiments, measurements of rotation (such as GCG measurements, for example) may be less susceptible to artefacts when compared to measurements of linear movement (such as SCG, for example). However, in other embodiments, measurements of linear movement may be less susceptible to artefacts when compared to measurements of rotation. Further, in some embodiments, certain heart diseases, movement, or other external factors may deteriorate some but not all of the measurements in some segments. Also, in some embodiments, some of the measurements in some cycles may not have clear and/or accurate characteristic points (for example due to disease, movement, or external factors, or for example due to the inherent limitations of the measurements themselves), but others of the measurements may have related clear and accurate characteristic points. Therefore, in some embodiments, measuring both rotation (such as GCG measurements, for example) and linear movement (such as SCG, for example) may allow for increased opportunities for identifying time intervals or otherwise for analysis when compared to analyses that do not include measurements of both rotation and linear movement.

The sensor apparatus 102 is an example only, and alternative embodiments may include alternatives to the at least one movement sensor 122 and to the at least one reference movement sensor 126. Further, in some embodiments, the movement isolation layer 120, the at least one reference movement sensor 126, and/or the layer 128 may be omitted. Still further, as indicated above, some embodiments may omit an ECG sensor, and such embodiments may include one or more movement sensors such as the movement sensors described above, such as an SCG, a CGC, or both an SCG and a CGC, for example.

In some embodiments, one or more measurements from the pulse oximeter 118 may, in combination with other measurements such as those described herein, allow a blood pressure of the subject 110 to be inferred, estimated, and/or measured. For example, in some embodiments, a blood pressure of the subject 110 may be inferred, estimated, and/or measured from a combination of ECG measurements, SCG measurements (such as measurements of linear acceleration or linear movement, for example), and GCG measurements (such as measurements of rotational velocity or rotational movement, for example).

In summary, the sensor apparatus 102 may include one or more heart characteristic sensors (such as one or more of the capacitive sensor 112, the force-sensing resistor 114, the pulse oximeter 118, the at least one movement sensor 122, and/or the at least one reference movement sensor 126) that may measure electrical and/or mechanical characteristics of a heart of a subject, such as a human subject for example, and the sensor apparatus 102 may thus be referred to as an "electromechanical cardiograph" or as an "EMCardiograph".

Figure 4:
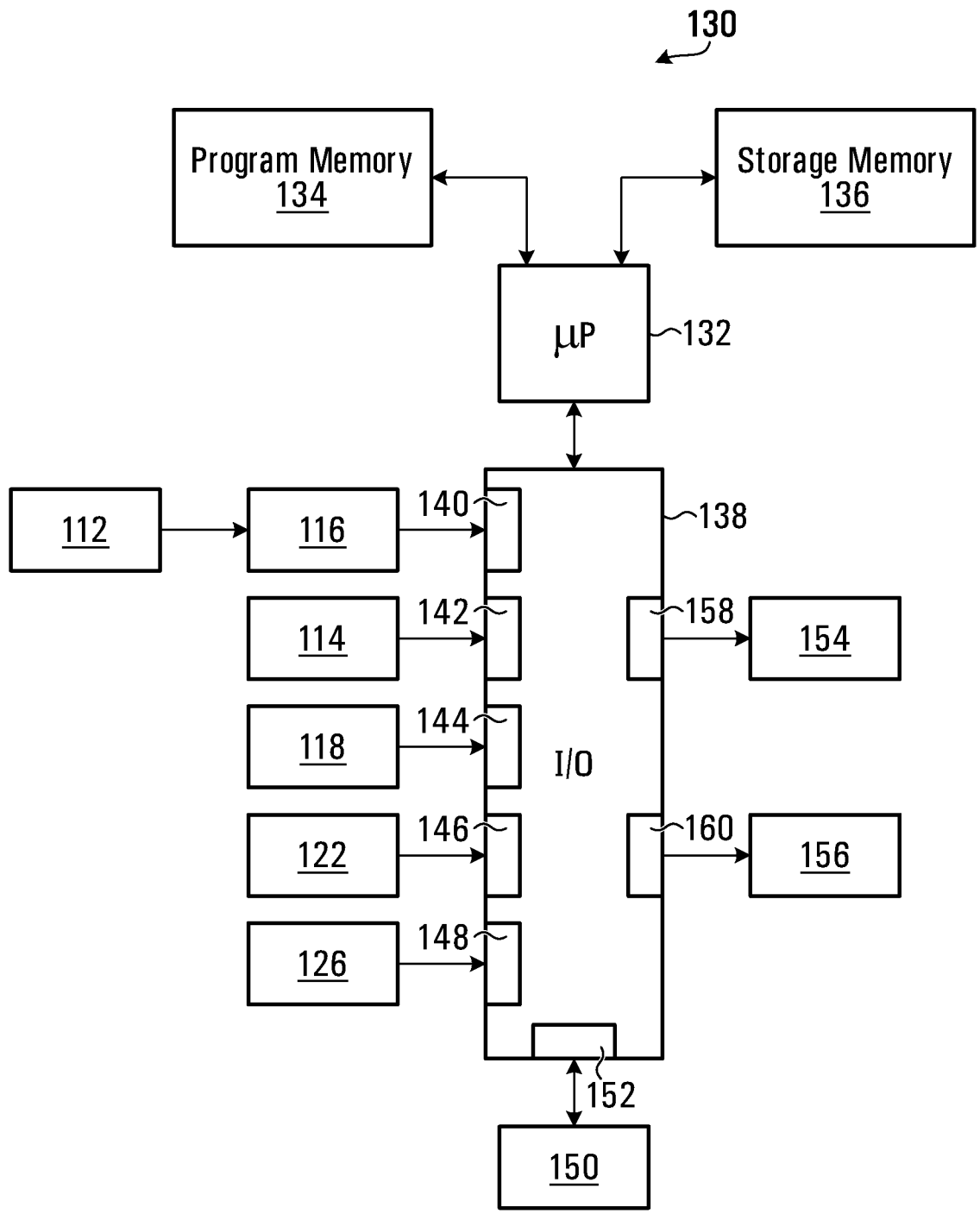
FIG. 4 illustrates a processor circuit of the sensor apparatus of FIG. 2.

Referring to FIGS. 3 and 4, the sensor apparatus 102 also includes a processor circuit shown generally at 130. The processor circuit 130 includes a central processing unit ("CPU") or microprocessor 132, and a program memory 134, a storage memory 136, and an input/output ("I/O") module 138 all in communication with the microprocessor 132. In general, the program memory 134 stores program codes that, when executed by the microprocessor 132, cause the processor circuit 130 to implement functions of the sensor apparatus 102. Further, in general, the storage memory 136 includes stores for storing storage codes as described herein for example. The program memory 134 and the storage memory 136 may be implemented in one or more of the same or different computer-readable storage media, which in various embodiments may include one or more of a read-only memory ("ROM"), random access memory ("RAM"), a hard disc drive ("HDD"), and other computer-readable and/or computer-writable storage media.

The I/O module 138 may include various signal interfaces, analog-to-digital converters ("ADCs"), receivers, transmitters, and/or other circuitry to receive, produce, and transmit signals as described herein, for example.

In the embodiment shown, the I/O module 138 includes an ECG input signal interface 140 for receiving amplified input signals from the amplifier 116 of ECG voltages measured by the capacitive sensor 112. The I/O module 138 also includes a force input signal interface 142 for receiving input signals from the force-sensing resistor 114 representing a force by which the sensor side 108 of the sensor apparatus 102 is held against the subject 110. The I/O module 138 also includes a pulse oximeter input signal interface 144 for receiving input signals from the pulse oximeter 118 representing pulse rate and/or oxygen saturation of the blood of the subject 110. The I/O module 138 also includes a movement input signal interface 146 for receiving input signals from the at least one movement sensor 122 representing movement of the sensor side 108 of the sensor apparatus 102 caused by movement of the heart of the subject 110. The I/O module 138 also includes a reference movement input signal interface 148 for receiving input signals from the at least one reference movement sensor 126 representing movement of the layer 126 of the sensor apparatus 102.

As shown in FIG. 1, the sensor apparatus 102 also includes a radio-signal transceiver 150, and the I/O module 138 also includes a radio signal interface 152 for causing the radio-signal transceiver 150 to transmit signals, and for receiving input signals from the radio-signal transceiver 150, as described herein for example. In some embodiments, the radio signal interface 152 may cause the radio-signal transceiver 150 to transmit and/or receive signals using a Bluetooth™ protocol or a different protocol, for example.

The sensor apparatus 102 also includes a visible output 154 and an audible output 156 for producing visible and audible outputs respectively. The I/O module 138 also includes a visible output signal interface 158 for producing and transmitting signals for causing the visible output 154 to produce visible outputs, and the I/O module 138 also includes an audible output interface 160 for producing and transmitting signals for causing the audible output 156 to produce audible outputs.

The I/O module 138 is an example only and may differ in alternative embodiments. For example, alternative embodiments may include more, fewer, and/or different input interfaces and/or more, fewer, and/or different output interfaces. Also, in alternative embodiments, one or both of the visible output 154 and the audible output 156 may be omitted or varied.

More generally, the processor circuit 130 is an example only, and sensor apparatuses according to other embodiments may vary. For example, in alternative embodiments, the sensor apparatus 102 may include different hardware and/or software, which may include more than one microprocessor, one or more alternatives to the microprocessor 132, discrete logic circuits, or an application-specific integrated circuit ("ASIC"), or combinations of one or more thereof, for example.

More generally, the sensor apparatus 102 is an example only, and sensor apparatuses according to other embodiments may vary. For example, in alternative embodiments, a sensor apparatus may include more sensors, fewer sensors, or different sensors than the sensor apparatus 102. As one example, alternative embodiments may include a phonocardiograph that may measure heart sounds in addition to other sensors such as some or all of the other sensors described herein, for example.

Referring back to FIG. 1, the local computing device 104 includes a radio-signal transceiver 161 operable to communicate with the sensor apparatus 102 by transmitting radio signals to, and by receiving radio signals from, the radio-signal transceiver 150. As indicated above, in some embodiments, the radio signal interface 152 may cause the radio-signal transceiver 150 to transmit and/or receive signals using the Bluetooth™ protocol or a different protocol, for example, and in such embodiments the radio-signal transceiver 161 may also transmit and/or receive signals using the Bluetooth™ protocol or the different protocol, for example. Further, the local computing device 104 may communicate with the remote computing device 106 over a computer network 163, such as the Internet for example. However, the radio-signal transceivers 150 and 161 are examples only, and alternative embodiments may involve other types of communication between the sensor apparatus 102 and the local computing device 104. Such other types of communication may include other types of wireless communication, communication using one or more wires, or communication using one or more portable storage devices, for example.

Figure 5:
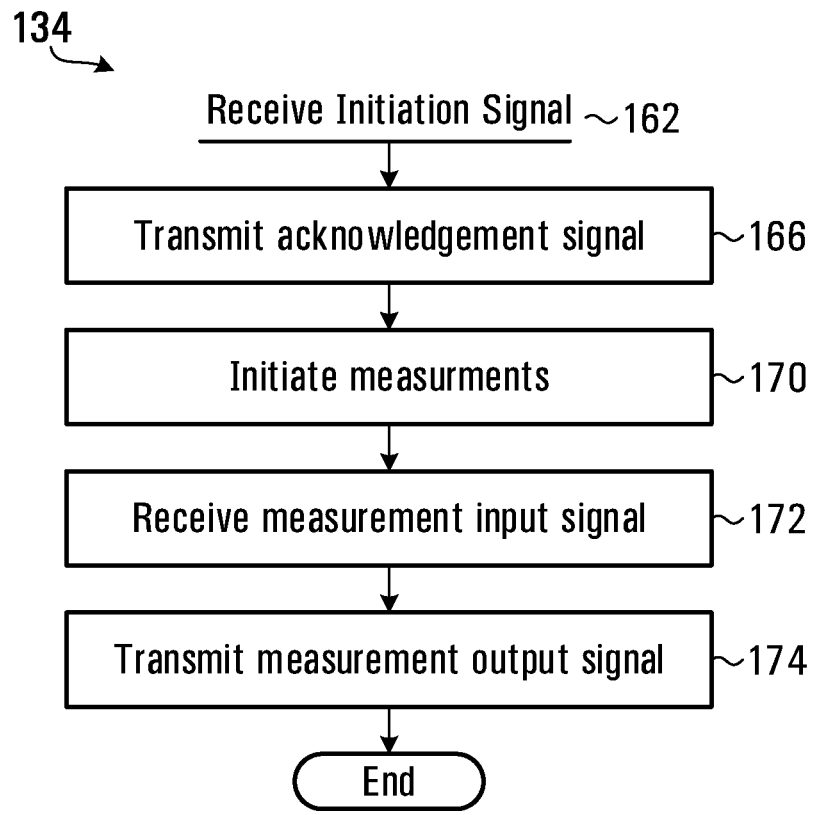
FIG. 5 illustrates blocks of code in a program memory of the processor circuit of FIG. 4.
Figure 6:
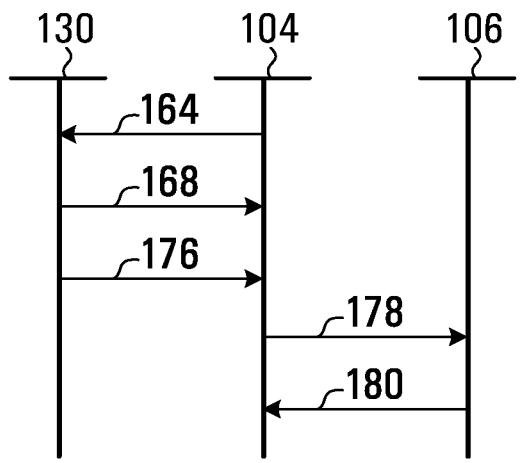
FIG. 6 illustrates an exchange of signals according to another embodiment.

In the embodiment shown, a user may initiate a method that involves causing the sensor apparatus 102 to measure at least one measurement of at least one characteristic of a heart of a subject. Referring to FIGS. 4, 5, and 6, program codes in the program memory 134 are illustrated schematically and begin at 162 when the processor circuit 130 receives an initiation signal 164 from the local computing device 104, for example in response to user interaction with the local computing device 104. The program codes in the program memory 134 continue at block 166, which includes code for directing the microprocessor 132 to cause the radio-signal transceiver 150 to transmit an acknowledgement signal 168 to the radio-signal transceiver 161 of the local computing device 104.

The program codes in the program memory 134 then continue at block 170, which includes codes for directing the microprocessor 132 to cause measurement devices of the sensor apparatus 102 to measure at least one characteristic of the heart of the subject 110. For example, in the embodiment shown, the codes of block 170 cause the microprocessor 132 to cause the capacitive sensor 112 to measure a time series of ECG measurements of the heart of the subject 110 during a period of time, cause the pulse oximeter 118 to measure oxygen pulse rate and/or saturation in the blood of the subject 110 during a period of time, and cause the at least one movement sensor 122 and the at least one reference movement sensor 126 to measure movement caused by the heart of the subject 110 during a period of time. The periods of time may be the same, or may be different, and may be overlapping in some embodiments. In some embodiments, the periods of time may be synchronized within about 4 milliseconds ("ms") or within about 5 ms of each other, or within 0 ms of each other. In some embodiments, the periods of time may be determined by the local computing device 104 based on requirements for one or more pre-designed physiological tests, and may range from about 30 seconds to about 60 seconds, for example. Further, as indicated above, some embodiments may omit the pulse oximeter 118.

As indicated above, the capacitive sensor 112 together with the rest of the sensor apparatus 102 may, in some embodiments, be held against a subject rather than being adhered to the subject. As a result, it is possible that the sensor apparatus 102 could be held with too little force (for example, too little force to enable the at least one movement sensor 122 to measure movement caused by the heart of the subject 110) or with too much force (for example, enough force to interfere with and/or corrupt measurements by introducing artefacts, for example).

Therefore, while the measurement devices of the sensor apparatus 102 to measure the at least one characteristic of the heart of the subject 110 in response to the codes at block 170, and/or at one or more other times, the processor circuit 130 may determine whether a force by which the sensor side 108 of the sensor apparatus 102 is held against the subject 110 is within a range between a minimum force and a maximum force or otherwise satisfies a criterion. For example, the storage memory 136 may store codes representing a minimum force and a maximum force. Such a minimum force and such a maximum force may define a range of forces by which the sensor side 108 of the sensor apparatus 102 is held against the subject 110 that may be acceptable for accurate measurements as described herein, for example.

In some embodiments, such a minimum force may be a force sufficient to maintain a position of the sensor side 108 of the sensor apparatus 102 against the subject 110, for example. Also, in some embodiments, such a maximum force may be about 300 Newtons, for example. However, such a minimum force and such a maximum force may vary in different embodiments, and may depend on types of one or more heart characteristic sensors in different embodiments.

At one or more times, for example initially, repeatedly, periodically, and/or at regular intervals while the measurement devices of the sensor apparatus 102 to measure the at least one characteristic of the heart of the subject 110 in response to the codes at block 170, the processor circuit 130 may determine whether a force, indicated by one or more input signals received at the input signal interface 142 from the force-sensing resistor 114, by which the sensor side 108 of the sensor apparatus 102 is held against the subject 110 is between the minimum force and the maximum force according to codes stored in the storage memory 136. At such a time, if the force is less than the minimum force or greater than the maximum force, or if otherwise the force does not satisfy a criterion, the microprocessor 132 may suspend measurement of the at least one characteristic of the heart of the subject 110 in response to the codes at block 170 until the force is between the minimum force and the maximum force. Also, at such a time, if the force is less than the minimum force or greater than the maximum force, or if otherwise the force does not satisfy a criterion, the microprocessor 132 may cause the sensor apparatus 102 to produce at least one force output signal, for example by causing the visible output 154 to produce a visible output and/or by causing the audible output 156 to produce an audible output.

Alternative embodiments may differ. For example, in some embodiments, the local computing device 104 and/or one or more other devices may determine whether the force by which the sensor side 108 of the sensor apparatus 102 is held against the subject 110 is within a range between a minimum force and a maximum force or otherwise satisfies a criterion. As another example, the sensor apparatus 102, the local computing device 104, and/or one or more other devices may produce at least one force output signal that may be visible, audible, and/or otherwise discernible.

Therefore, embodiments such as those described herein may produce at least one force output signal that may alert a user if a force by which a sensor side of the sensor apparatus 102 is held against a subject is outside of a range between a minimum force and a maximum force or otherwise does not satisfy a criterion. Such an alert may facilitate measurements as described herein for example by allowing a user to adjust force as may be necessary, and as one example, such an alert may facilitate measurements (as described herein for example) during exercise.

During or after measurement of the at least one characteristic of the heart of the subject 110 in response to the codes at block 170, the processor circuit may receive input measurement signals. Therefore, during or after block 170, the program codes in the program memory 134 continue at block 172, which includes codes for directing the microprocessor 132 to receive input measurement signals. For example, the codes at block 172 may cause the microprocessor 132 to receive: at the ECG input signal interface 140, amplified input signals from the amplifier 116 of ECG voltages measured by the capacitive sensor 112; at the force input signal interface 142, input signals from the force-sensing resistor 114 representing a force by which the sensor side 108 of the sensor apparatus 102 is held against the subject 110; at the pulse oximeter input signal interface 144, input signals from the pulse oximeter 118 representing pulse rate and/or oxygen saturation of the blood of the subject 110; at the movement input signal interface 146, input signals from the at least one movement sensor 122 representing movement of the sensor side 108 of the sensor apparatus 102 caused by movement of the heart of the subject 110; and/or, at the reference movement input signal interface 148, input signals from the at least one reference movement sensor 126 representing movement of the layer 128 of the sensor apparatus 102. Further, the codes at block 172 may cause the processor circuit 130 to digitize, store, and/or packetize (for transmission purposes, for example) some or all of the input measurement signals.

In some embodiments, the sensor apparatus 102 may be used for long-term, periodic, prolonged, and/or repeated measurements. Also, in some embodiments, the sensor apparatus 102 may be used outside of communication range from the local computing device 104. In such embodiments, or in other embodiments, the processor circuit 130 may be configured (by one or more configuration signals from the local computing device 104, for example) so that the codes at block 172 cause the microprocessor 132 to store some or all of the input measurement signals in the storage memory 136, for example for later retrieval by or transmission to the local computing device 104.

In some embodiments, some or all of the input measurement signals may indicate whether the sensor apparatus 102 is appropriately oriented and/or positioned. For example, in some embodiments, the sensor apparatus 102, the local computing device 104, the remote computing device 106, and/or one or more other computing devices may analyze some or all of the input measurement signals, and/or one or more signals and/or values that may be derived from some or all of the input measurement signals, to determine whether the sensor apparatus 102 appears to be appropriately oriented and/or positioned. Such determinations may be at one or more times, for example initially, repeatedly, periodically, and/or at regular intervals while the measurement devices of the sensor apparatus 102 to measure the at least one characteristic of the heart of the subject 110 in response to the codes at block 170. In such embodiments, the codes at block 172 may cause the processor circuit 130 to alert a user if the sensor apparatus 102 appears not to be appropriately oriented and/or positioned. More generally, in such embodiments, the sensor apparatus 102, the local computing device 104, and/or one or more other devices may produce at least one output signal that may be visible, audible, and/or otherwise discernible and that may facilitate alerting a user if the sensor apparatus 102 appears not to be appropriately oriented and/or positioned.

The program codes in the program memory 134 then continue at block 174, which includes codes for directing the microprocessor 132 to cause the radio-signal transceiver 150 to transmit, to the radio-signal transceiver 161 and thus to the local computing device 104, at least one measurement output signal 176. The local computing device 104 may then transmit at least one measurement output signal 178 to the remote computing device 106, for example over the computer network 163. The at least one measurement output signal 176 and the at least one measurement output signal 178 may include some or all of the input measurement signals received at block 172, or may include other signals derived from or otherwise representing some or all of the input measurement signals received at block 172.

The remote computing device 106 may infer one or more inferences from the at least one measurement output signal 178. Such inferences may include, for example, an inference of a likelihood of a heart condition or disease (such as coronary artery disease ("CAD") or atrial fibrillation ("AFib"), for example). As described below, for example, such inferences may facilitate screening subjects for cardiac abnormality and subsequently making further suggestions about the cause of abnormality based on timing, rhythm, and force metrics, for example.

The remote computing device 106 may then transmit, to the local computing device 104, at least one inference indication signal 180 indicating any inferences that the remote computing device 106 may have inferred from the at least one measurement output signal 178. The local computing device 104 may then produce at least one inference output signal (for example at a signal interface 181 of the local computing device 104) indicating, to a user of the local computing device 104, any inferences that the remote computing device 106 may have inferred from the at least one measurement output signal 178. In alternative embodiments, the at least one inference output signal need not be produced by the local computing device 104, and may be produced by the sensor apparatus 102 or by still another device. In general, the at least one inference output signal may cause a visible, audible, and/or otherwise discernible indication to be presented (by the sensor apparatus 102, by the local computing device 104, and/or by one or more other devices) to a user to indicate any inferences to the user. Further, some or all of the measurements represented by the at least one measurement output signal 178, and/or some or all of any inferences, may be stored in memory by the sensor apparatus 102, by the local computing device 104, by the remote computing device 106, and/or by one or more other devices.

Alternative embodiments may vary. For example, sensor apparatuses such as those described herein may be stand-alone units that may be held to a subject, or may be embedded inside another product such as a smartphone, a smartphone case, a watch, or a smartwatch. In some such embodiments, the sensor apparatus 102 and the local computing device 104 may be combined into a single device.

As another example, sensor apparatuses such as those described herein may be held by hand or held by a strap, belt, garment, or other means, for example. Any such sensor apparatus may include a force sensor (such as the force-sensing resistor 114, for example) that may measure a force by which a sensor side of the sensor apparatus, and any such sensor apparatus (or another device) may produce at least one force output signal if the force is less than a minimum force or greater than a maximum force or otherwise does not satisfy a criterion.

Figure 7:
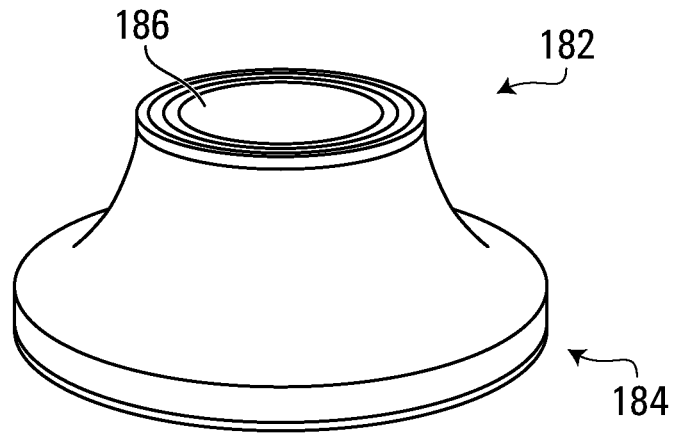
FIG. 7 illustrates a sensor apparatus according to another embodiment.

As one example, a sensor apparatus according to another embodiment is shown generally at 182 in FIG. 7. The sensor apparatus 182 is a hand-holdable, standalone device having a sensor side shown generally at 184 and positionable against a subject such as the subject 110, for example. Opposite the sensor side 184, the sensor apparatus 182 includes a visible output 186 that may be similar to the visible output 154 described above, for example. Otherwise the sensor apparatus 182 may be similar to the sensor apparatus 102.

Figure 8:
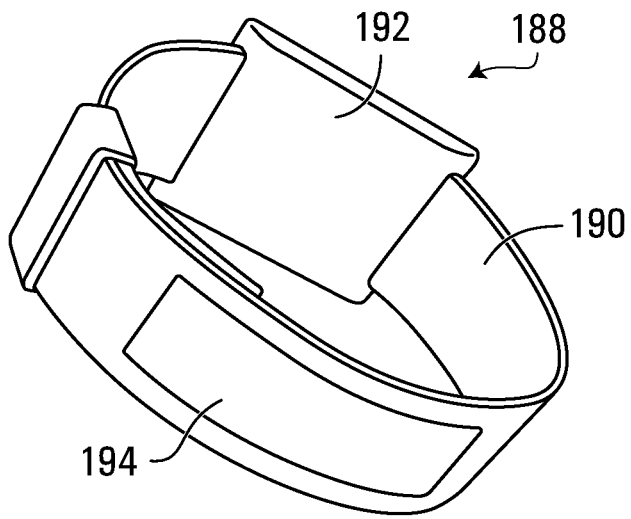
FIG. 8 illustrates a sensor apparatus according to another embodiment.

As another example, a sensor apparatus according to another embodiment is shown generally at 188 in FIG. 8. The sensor apparatus 188 includes a wristband 190 and a smartwatch or other user-interface portion 192. The wristband 190 includes a capacitive sensor 194 that may be embedded in the wristband 190 and that may function as an ECG sensor similar to the capacitive sensor 112 as described above for example, so that a subject wearing the sensor apparatus 188 on a wrist of the subject may place the capacitive sensor 194 against the subject. The user-interface portion 192 may include other sensors and a processor circuit, and in general the sensor apparatus 188 may be similar to the sensor apparatus 102.

Although the embodiment of FIG. 8 includes a smartwatch or other user-interface portion 192, some embodiments may include a wristband (or another body, for example) including one or more heart characteristic sensors, and the wristband need not be coupled to or associated with any particular user-interface portion or other computing device. Therefore, some embodiments may include one or more heart characteristic sensors, such as those described herein for example, on a wristband or on another body, for example, and such embodiments need not include any smartwatch, any other user-interface portion, or any other computing device. Such embodiments may also include at least one signal interface to transmit at least one measurement output signal (which may, for example, represent a time series of ECG measurements, a time series of measurements of movement, other measurements, or a combination of two or more thereof) to at least one computing device (such as a smartwatch or one or more other computing devices, for example) separate from the sensor apparatus.

Figure 9:
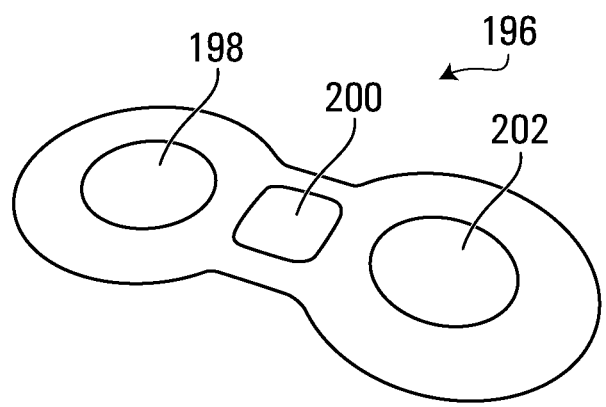
FIG. 9 illustrates a sensor apparatus according to another embodiment.

As another example, a sensor apparatus according to another embodiment is shown generally at 196 in FIG. 9 and may be configured as a sensor plate that may be attached to a smartphone case, for example. The sensor apparatus 196 includes capacitive sensors 198, 200, and 202 that may function as ECG sensors similar to the capacitive sensor 112 as described above for example, and otherwise the sensor apparatus 196 may be similar to the sensor apparatus 102.

More generally, the sensor system 100 is an example only, and alternative embodiments may differ. For example, in some embodiments, structures and/or functions (such as those described herein) of the sensor apparatus 102 may be embodied in one or more apparatuses that may differ from the sensor apparatus 102. As another example, in some embodiments, structures and/or functions (such as those described herein) of the local computing device 104 may be embodied in one or more apparatuses that may differ from the local computing device 104. As another example, in some embodiments, structures and/or functions (such as those described herein) of the remote computing device 106 may be embodied in one or more apparatuses that may differ from the remote computing device 106. As another example, in some embodiments, structures and/or functions (such as those described herein) of the sensor apparatus 102 and of the local computing device 104 may be embodied in one apparatus or in more than one other apparatus. As another example, in some embodiments, structures and/or functions (such as those described herein) of the local computing device 104 and of the remote computing device 106 may be embodied in one apparatus or in more than one other apparatus. As another example, in some embodiments, structures and/or functions (such as those described herein) of the sensor apparatus 102, of the local computing device 104, and of the remote computing device 106 may be embodied in one apparatus or in more than one other apparatus.

For example, some embodiments may include a sensor apparatus and at least one computing device without necessarily involving a local computing device and a remote computing device as described above. For example, referring to FIG. 10, a sensor system according to another embodiment is shown generally at 204 and includes a sensor apparatus 206 and a computing device 208 separate from the sensor apparatus 206. The sensor apparatus 206 includes a radio-signal transceiver 210, and the computing device 208 includes a radio-signal transceiver 212. The sensor apparatus 206 and the computing device 208 may communicate with each other by sending and receiving radio signals using the radio-signal transceivers 210 and 212. Again, however, the radio-signal transceivers 210 and 212 are examples only, and alternative embodiments may involve other types of communication between the sensor apparatus 206 and the computing device 208. Again, such other types of communication may include other types of wireless communication, communication using one or more wires, or communication using one or more portable storage devices, for example.

Figure 10:
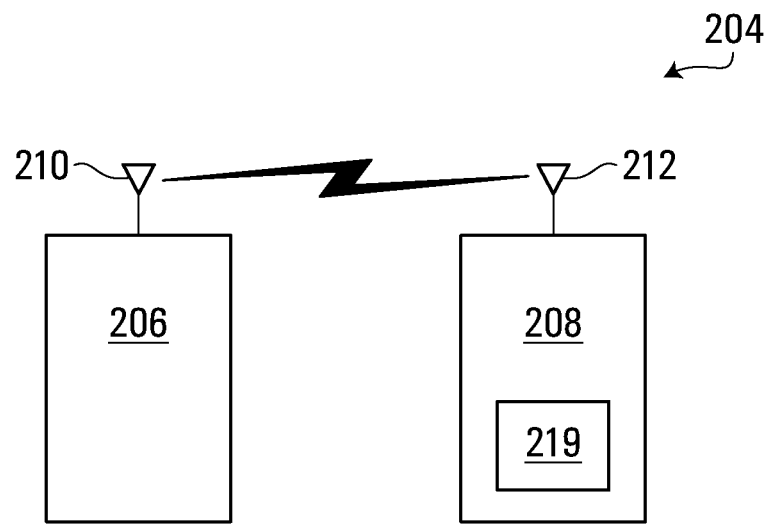
FIG. 10 illustrates a sensor system according to another embodiment.

In the embodiment shown in FIG. 10, the computing device 208 may infer one or more inferences from measurements by the sensor apparatus 206, so the embodiment shown in FIG. 10 may not require a remote computing device such as the remote computing device 106, or may interact with or involve a remote computing device differently than the embodiment shown in FIG. 1. Therefore, in the embodiment shown in FIG. 10, the sensor apparatus 206 and the computing device 208 may exchange signals as shown in FIG. 11, which is an alternative to the exchange of signals shown in FIG. 6.

Figure 11:
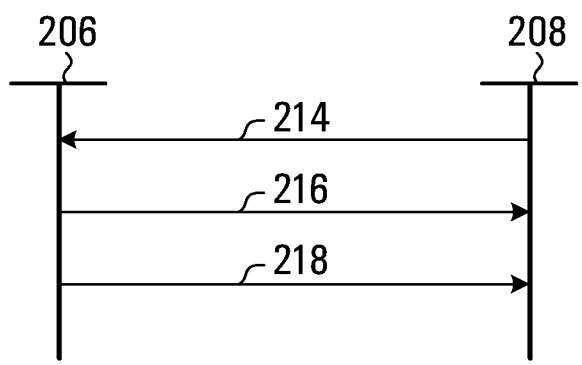
FIG. 11 illustrates an exchange of signals according to another embodiment.

As shown in FIG. 11, in the embodiment shown in FIG. 10, the computing device 208 may transmit an initiation signal 214 (which may be similar to the initiation signal 164, for example) to the sensor apparatus 206, and in response the sensor apparatus 206 may transmit an acknowledgement signal 216 (which may be similar to the acknowledgement signal 168, for example) to the computing device 208. Also in response to the initiation signal 214, the sensor apparatus 206 may cause measurement devices of the sensor apparatus 206 to measure at least one characteristic of a heart of a subject, as described above with reference to block 170, for example, and the sensor apparatus 206 may transmit at least one measurement output signal 218 (which may be similar to the at least one measurement output signal 176, for example) to the computing device 208. The computing device 208 may then infer one or more inferences from measurements by the sensor apparatus 206, and the computing device 208 may then produce (for example at a signal interface 219 of the computing device 208) at least one inference output signal indicating, to a user of the computing device 208, any inferences that the computing device 208 may have inferred from the at least one measurement output signal 218. Again, in alternative embodiments, the at least one inference output signal need not be produced by the computing device 208, and may be produced by the sensor apparatus 206 or by still another device.

Figure 12:
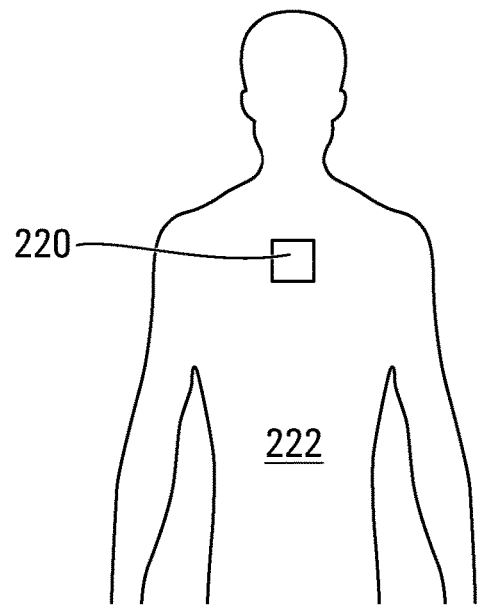
FIG. 12 illustrates a sensor position according to another embodiment.
Figure 13:
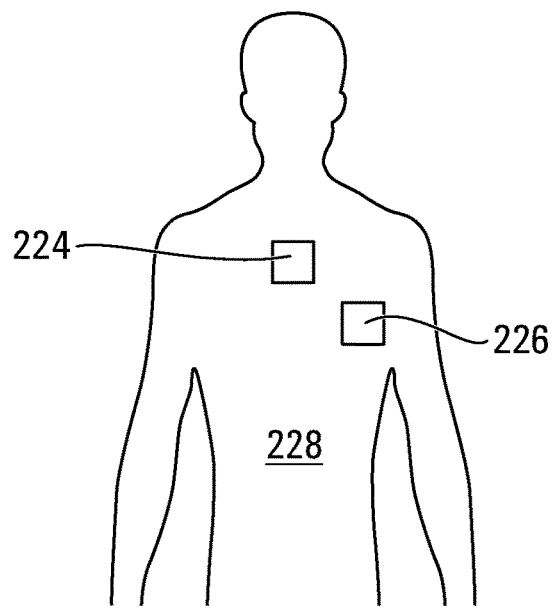
FIG. 13 illustrates sensor positions according to another embodiment.
Figure 14:
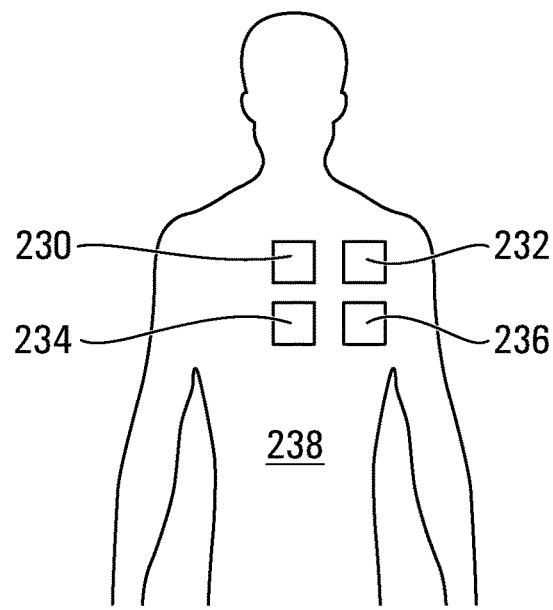
FIG. 14 illustrates sensor positions according to another embodiment.

Sensors such as those described herein may be positioned in one or more different positions on a subject. For example, FIG. 12 illustrates a sensor position 220 for a sensor on a subject 222 according to one embodiment. The sensor position 220 may be at or near a center of a sternum of the subject 222. As another example, FIG. 13 illustrates sensor positions 224 and 226 for one or more sensors on a subject 228 according to another embodiment. As another example, FIG. 14 illustrates sensor positions 230, 232, 234, and 236 for one or more sensors on a subject 238 according to another embodiment.

In summary, sensor apparatuses such as those described herein may noninvasively measure and record measurements of one or more electromechanical characteristics (such as linear acceleration, rotational velocity, and/or electrical activity, for example) of a heart of a subject (such as a human subject, for example), and sensor apparatuses such as those described herein may produce and transmit at least one measurement output signal to at least one computing device (such as the local computing device 104 or the computing device 208, for example). A computing device (such as the remote computing device 106 or the computing device 208, for example) may infer one or more inferences, for example of a likelihood of a heart condition or disease such as CAD or AFib, which may (as described below, for example) facilitate screening subjects for cardiac abnormality and subsequently making further suggestions about the cause of abnormality based on timing, rhythm, and force metrics, for example.

In some embodiments, systems such as those described above may be configurable in either a screening mode of operation or in a diagnostic mode of operation. In such embodiments, when the system is in the screening mode of operation, the at least one output signal to a user (as described above, for example) may represent one or more causes of cardiac abnormality without representing any particular cardiac disease. Also, in such embodiments, when the system is in the diagnostic mode of operation, the at least one output signal to a user (as described above, for example) may represent at least one particular cardiac disease. However, alternative embodiments may differ. For example, some embodiments may function only in a screening mode of operation as described above, or only in a diagnostic mode of operation. Still other embodiments may operate in one or more of the same or different modes of operation.

Sensor apparatuses such as those described herein may be used in different applications in different embodiments, which may involve measurements before, during, and/or after physical activity, and which may involve analyzing one or more signals representing measurements as described above, or may otherwise involve analyzing measurements as described above. In general, such measurements may represent electromechanical characteristics of a heart before, during, and/or after exercise or other physical activity. Further, parameters related to timing of cardiac events and the morphology of measurements of vibration may be extracted and/or may be used to design and develop one or more models to assess cardiac function, such as models described herein, for example.

B. Analysis of Electromechanical Characteristics

Figure 15:
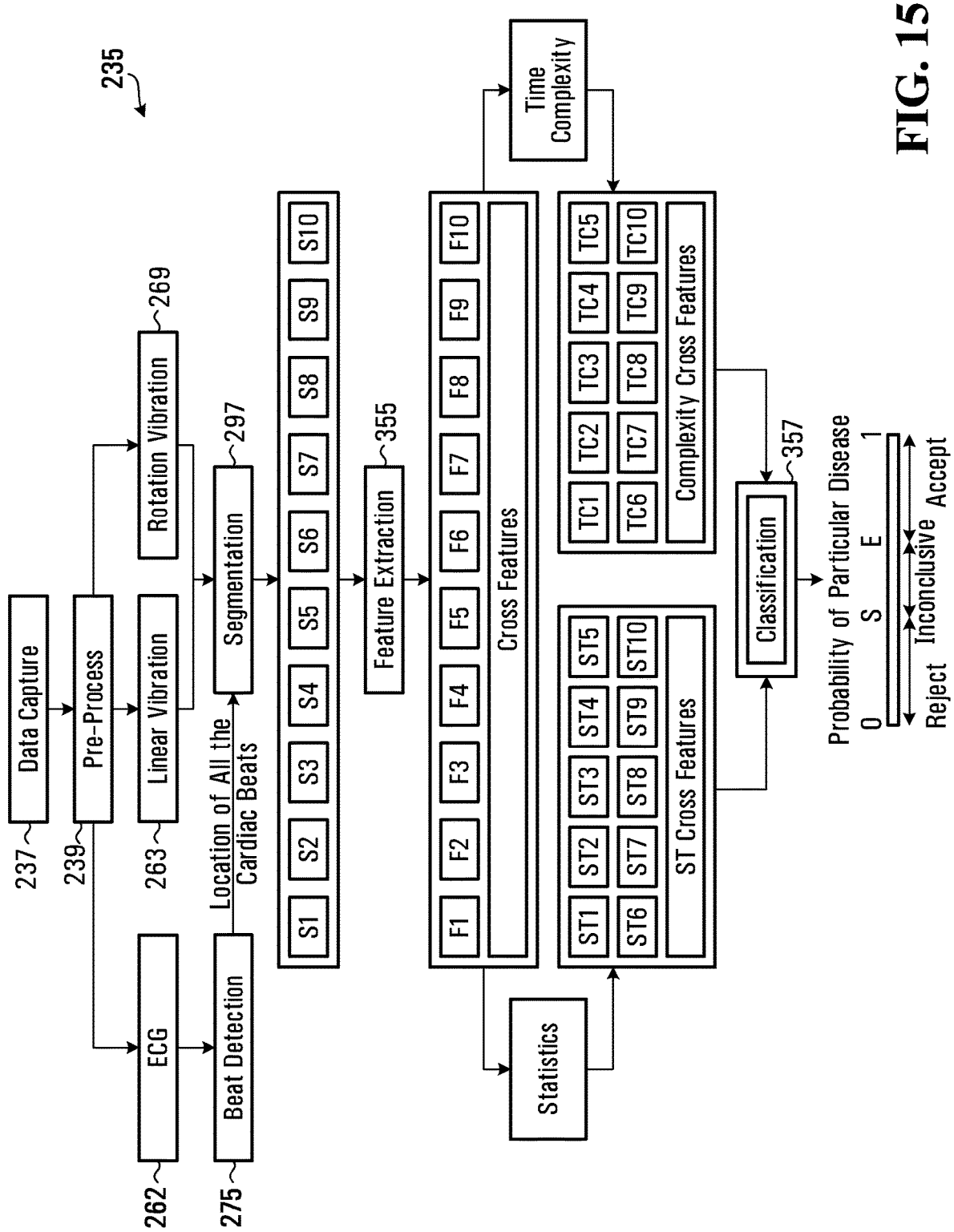
FIG. 15 illustrates a method, according to one embodiment, for sensing and analyzing electromechanical characteristics of a heart of a subject.

A method, according to one embodiment, for sensing and analyzing electromechanical characteristics of a heart of a subject is shown generally at 235 in FIG. 15 and may begin with measurements of electromechanical characteristics of the heart at 237. The measurements 237 may involve measurements as described above, for example. The method 235 may continue with data pre-processing 237, which may involve removing any baseline wander, noise, and/or artefacts, for example.

Figure 16:
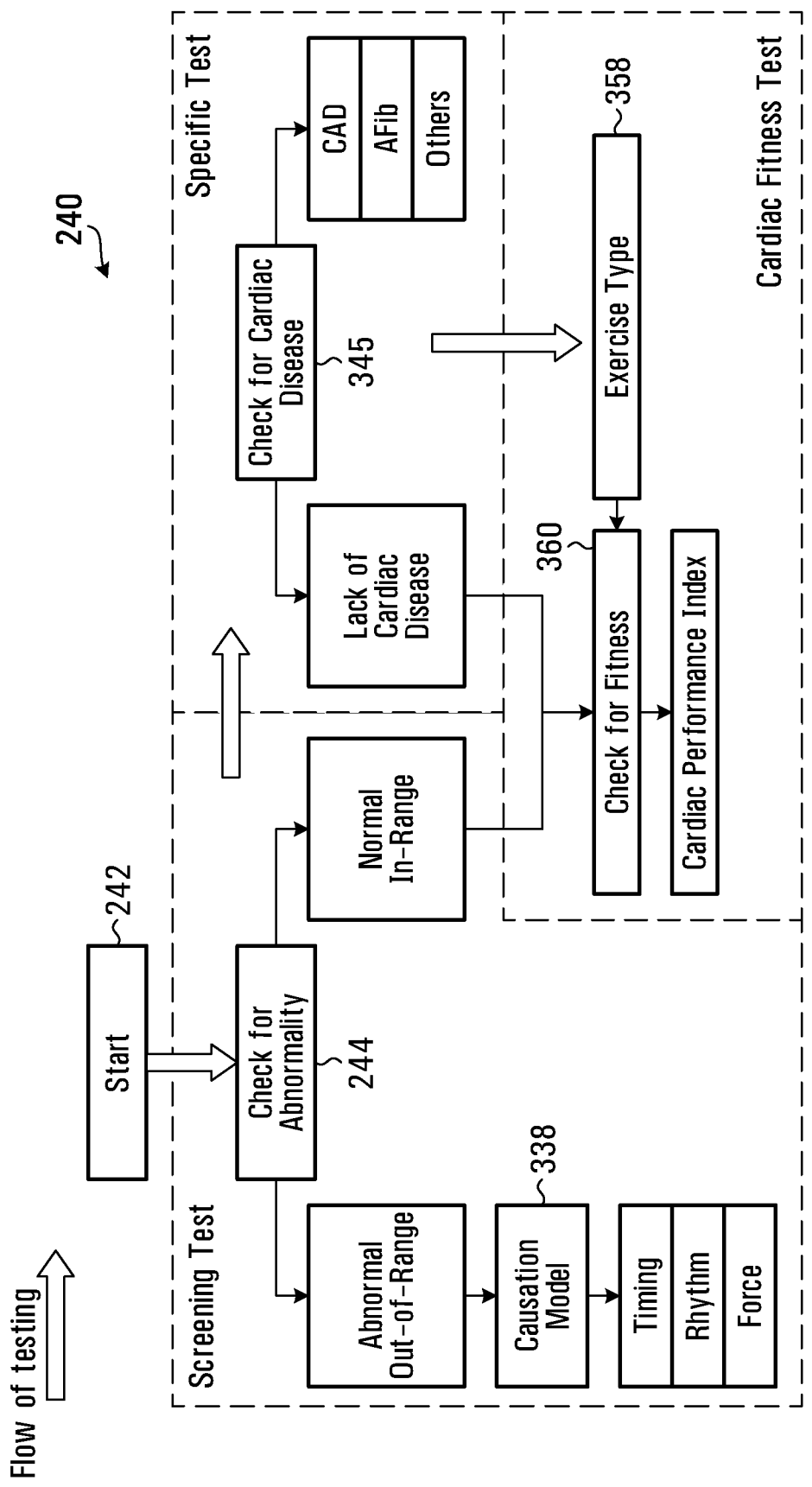
FIG. 16 illustrates a method, according to one embodiment, for sensing and analyzing electromechanical characteristics of a heart of a subject.

Another method, according to one embodiment, for sensing and analyzing electromechanical characteristics of a heart of a subject is shown generally at 240 in FIG. 16 and may begin at 242. In general, the methods 235 and 240 are examples only. Embodiments may include part or all of the method 235, include part or all of the method 240, or combinations thereof, and other embodiments may include additional steps and/or alternatives to steps as described herein. For example, the method 240 or other methods such as those described herein may include data pre-processing 237.

The method 240 may continue with a screening test (or functionality test) 244, which may generally involve screening a subject for one or more cardiac abnormalities. In some embodiments, the screening test 244 may be initiated by user interaction with a computing device (such as the local computing device 104 or the computing device 208 as described above, for example). In such embodiments, such a computing device may produce an initiation signal (such as the initiation signal 164 or 214 as described above, for example) and transmit the initiation signal to a sensor apparatus (such as the sensor apparatus 102, 182, 188, 196, or 206 as described above, for example). In response, such a sensor apparatus may measure electromechanical characteristics of a heart of a subject, and such a computing device may receive at least one measurement output signal (such as the at least one measurement output signal 176 or 218 as described above, for example).

In the embodiment shown, such electromechanical characteristics include time series of ECG, SCG, and GCG measurements of the heart of the subject. The SCG measurements may more generally be measurements of linear vibration, which may be measured as acceleration. Also, the GCG measurements may more generally be measurements of rotational vibration, which may be measured as angular velocity.

Alternative embodiments may differ. For example, in alternative embodiments, the screening test 244 may be initiated by user interaction directly with one or more sensor apparatuses (such as one or more of the sensor apparatus 102, 182, 188, 196, or 206 as described above, for example). In such embodiments, the initiation signal and/or the at least one measurement output signal may be omitted or may be internal to the sensor apparatus. Further, alternative embodiments may involve more than one sensor apparatus. Further, measurements in alternative embodiments may differ. For example, alternative embodiments may include different measurements of linear movement and/or different measurements of rotation. Further, some embodiments may include fewer, more, or different types of measurements.

In the screening test 244, the measurements of the electromechanical characteristics of the heart (whether indicated in at least one measurement output signal or otherwise) may be analyzed. In the following description of one embodiment, the remote computing device 106 analyzes the measurements of the electromechanical characteristics of the heart. However, the following description is an example only, and in alternative embodiments, for example, one or more sensor apparatuses, one or more other computing devices, or a combination thereof may analyze the measurements of the electromechanical characteristics of the heart.

Figure 17:
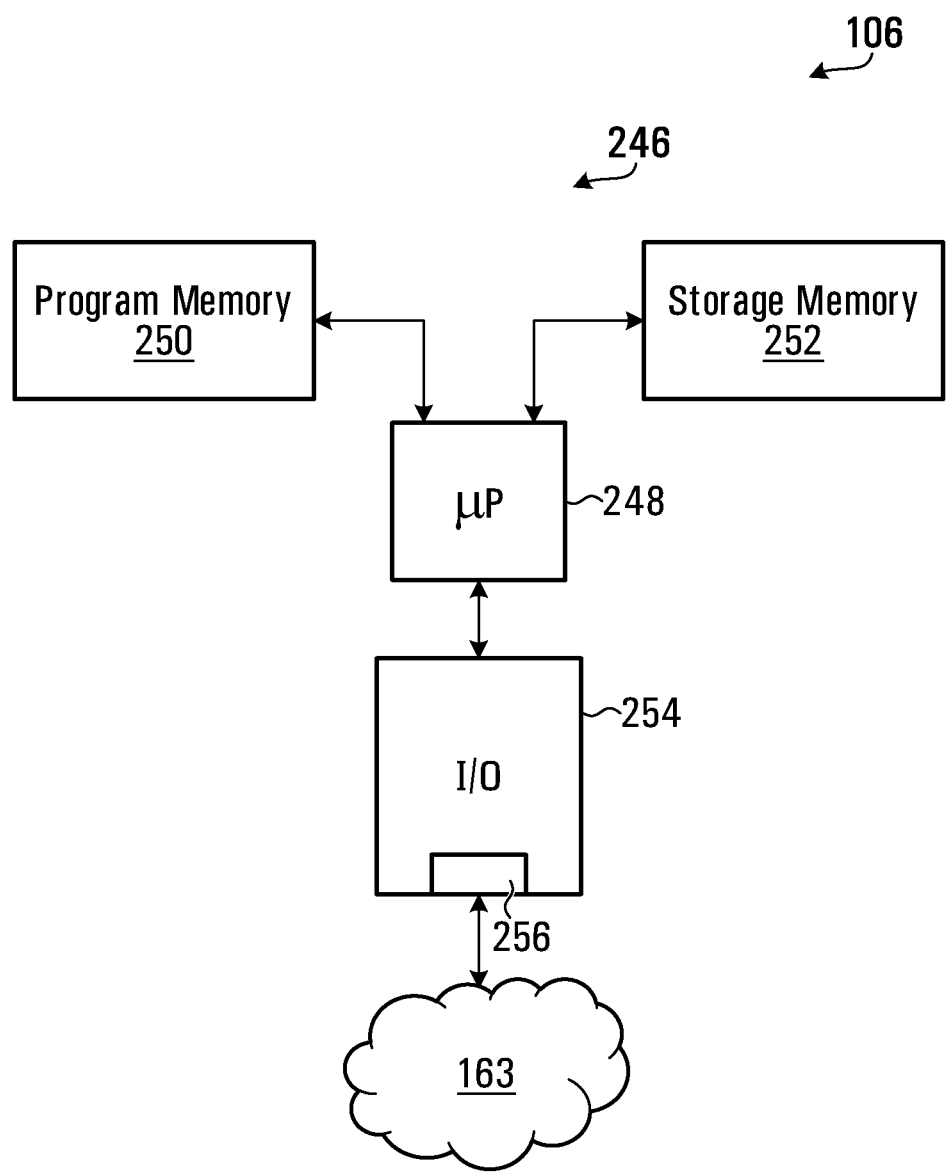
FIG. 17 illustrates a processor circuit of a remote computing device of the sensor system of FIG. 1.

Referring to FIGS. 1 and 17, the remote computing device 106 includes a processor circuit shown generally at 246. The processor circuit 246 includes a CPU or microprocessor 248, and a program memory 250, a storage memory 252, and an input/output ("I/O") module 254 all in communication with the microprocessor 248. In general, the program memory 250 stores program codes that, when executed by the microprocessor 248, cause the processor circuit 246 to implement functions of the remote computing device 106. Further, in general, the storage memory 252 includes stores for storing storage codes as described herein for example. The program memory 250 and the storage memory 252 may be implemented in one or more of the same or different computer-readable storage media, which in various embodiments may include one or more of a ROM, RAM, a HDD, and other computer-readable and/or computer-writable storage media.

The I/O module 254 may include various signal interfaces, ADCs, receivers, transmitters, and/or other circuitry to receive, produce, and transmit signals as described herein, for example. In the embodiment shown, the I/O module 254 includes a network signal interface 256 for transmitting output signals over, and for receiving input signals from, the computer network 163.

The processor circuit 246 is an example only, and computing devices according to other embodiments may vary. For example, in alternative embodiments, the remote computing device 106 may include different hardware and/or software, which may include more than one microprocessor, one or more alternatives to the microprocessor 248, discrete logic circuits, or an application-specific integrated circuit ("ASIC"), or combinations of one or more thereof, for example. Further, as indicated above, in alternative embodiments, one or more sensor apparatuses, one or more other computing devices, or a combination thereof may analyze the measurements of the electromechanical characteristics of the heart. Therefore, in alternative embodiments, such other apparatuses or devices may include processor circuits similar to the processor circuit 246, or one or more alternatives to such a processor circuit, for example.

Figure 18A:
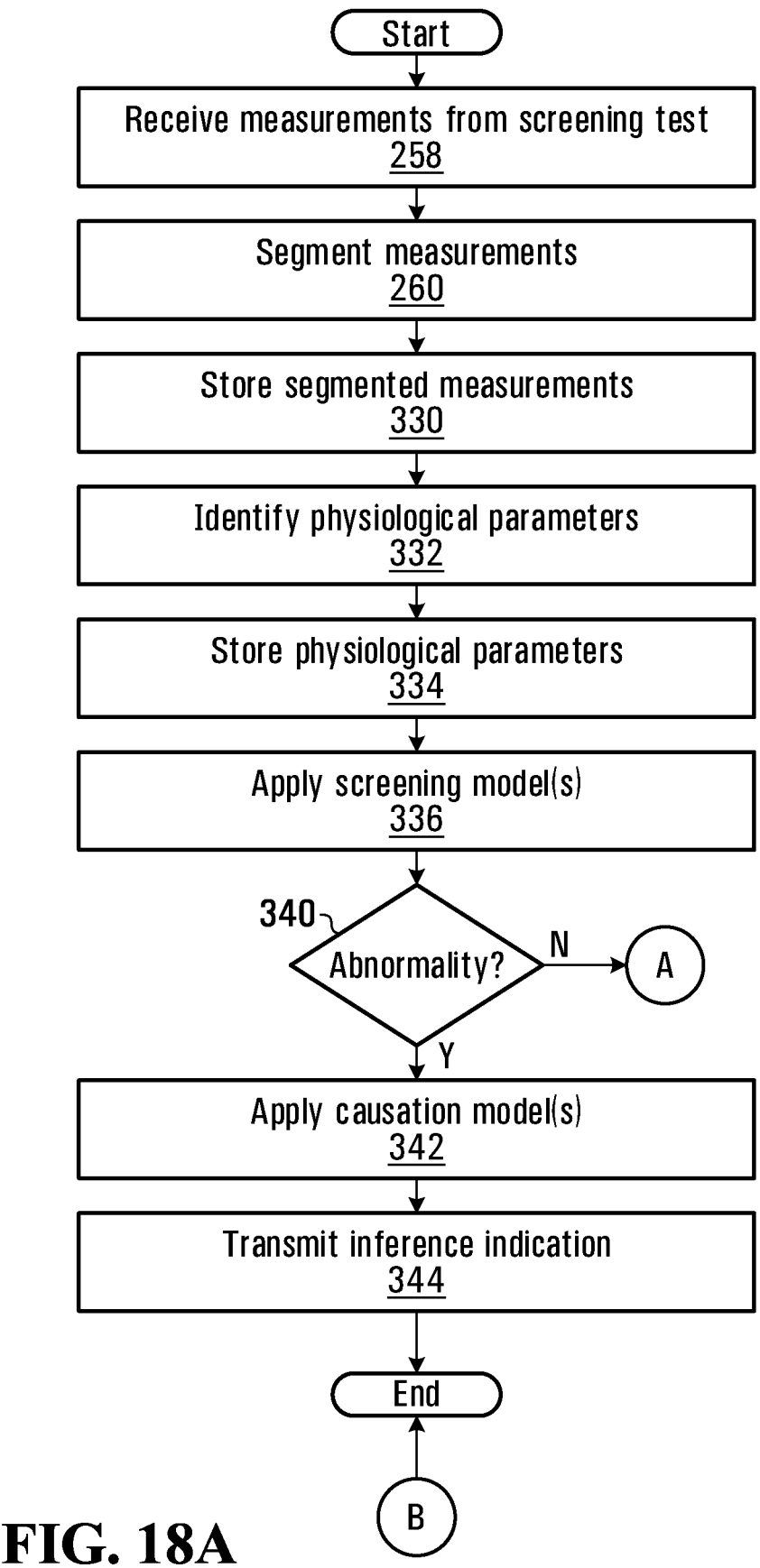
FIG. 18 illustrates blocks of code in a program memory of the processor circuit of FIG. 17.
Figure 18B:
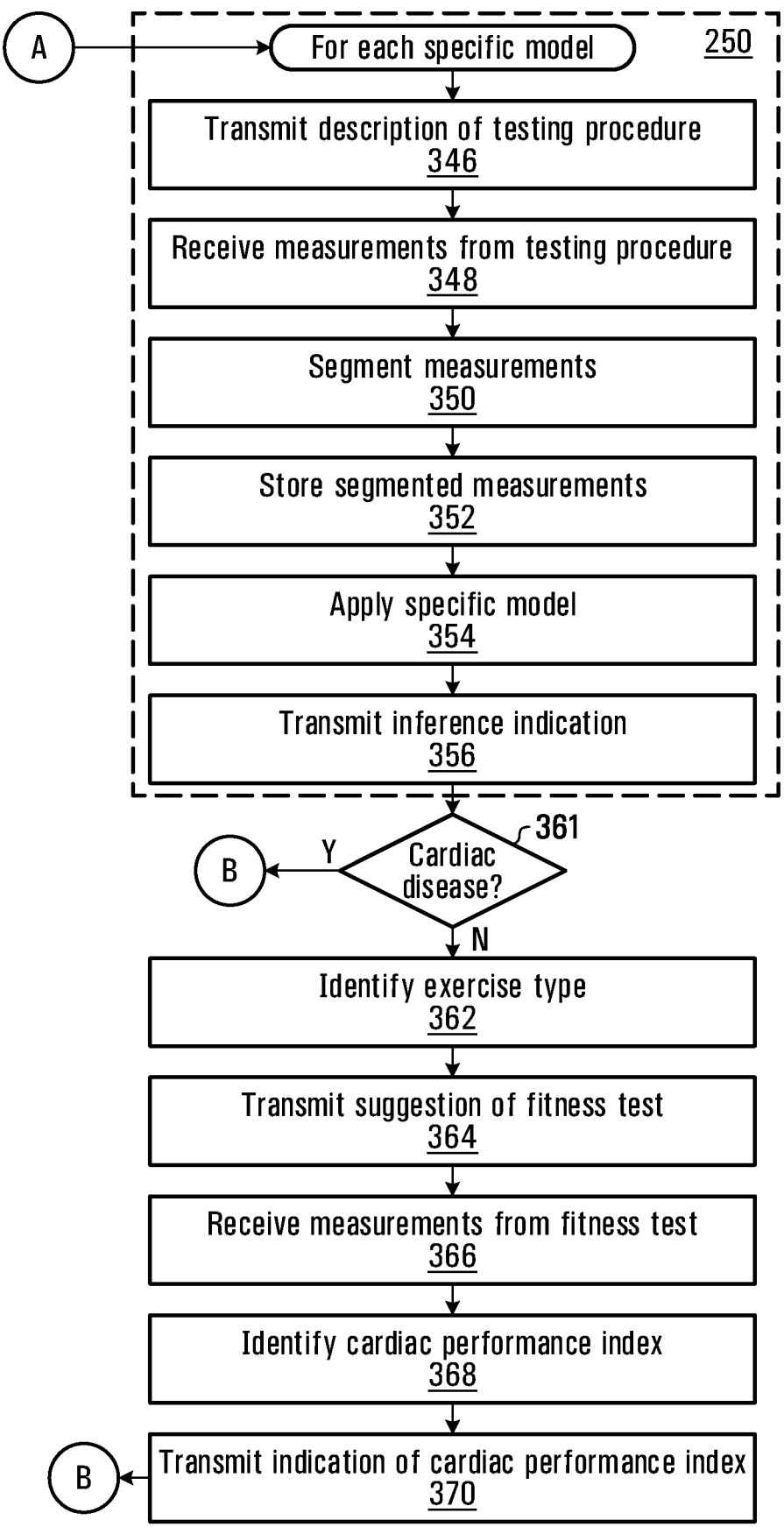

Referring to FIG. 18, program codes in the program memory 250 are illustrated schematically and begin at 258 when the processor circuit 246 receives the at least one measurement output signal 178 (shown in FIG. 6) or one or more other signals representing time series of measurements from a screening test by one or more sensor apparatuses (such as the sensor apparatus 102, for example). The program codes in the program memory 250 may continue at block 260, which includes code for directing the microprocessor 248 to segment the measurements indicated in the at least one measurement output signal received at block 258.

Figure 19:
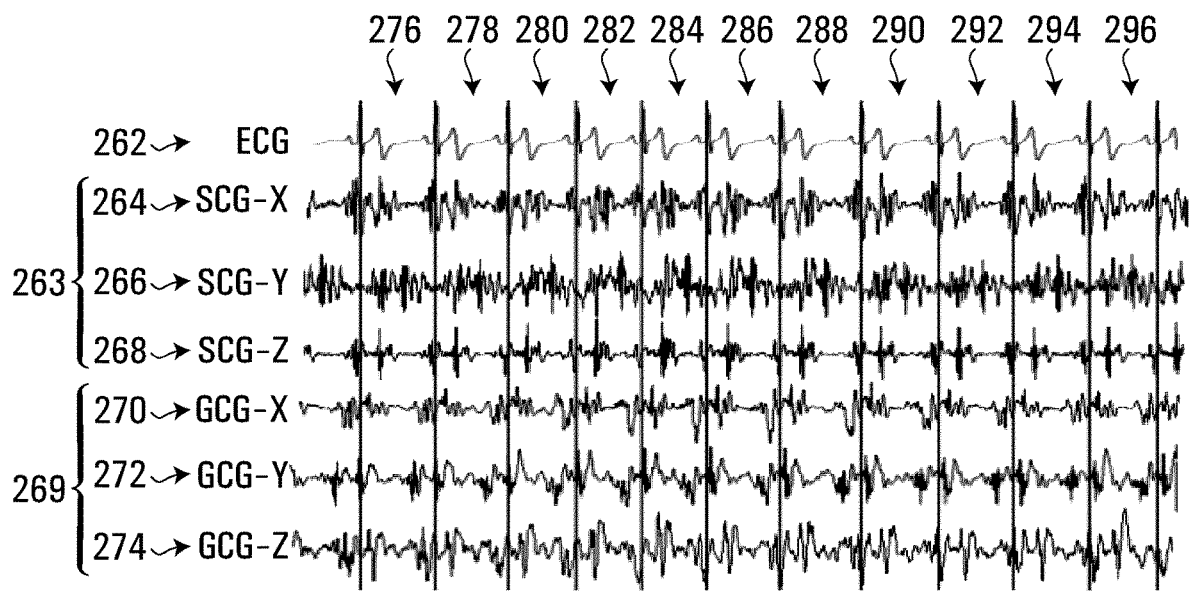
FIG. 19 illustrates an example of measurements of electromechanical characteristics of a heart of a subject according to one embodiment.

FIG. 19 illustrates an example of measurements of electromechanical characteristics of a heart of a subject according to one embodiment. The example of FIG. 19 includes a time series of ECG measurements of the heart shown generally at 262. The example of FIG. 19 includes a time series of SCG measurements of linear acceleration (or, more generally, linear movement) shown generally at 263 in three dimensions or directions.

In the embodiment shown, the time series of SCG measurements of linear acceleration 263 includes a component (that may be referred to as an "SCG-X" component) shown generally at 264 in an "x" dimension or direction. The "x" dimension or direction may be a left-to-right, side-to-side, or lateral-medial dimension or direction relative to the subject. In the embodiment shown, the time series of SCG measurements of linear acceleration 263 also includes a component (that may be referred to as an "SCG-Y" component) shown generally at 266 in a "y" dimension or direction. The "y" dimension or direction may be a head-to-toe or superior-inferior dimension or direction relative to the subject. In the embodiment shown, the time series of SCG measurements of linear acceleration 263 also includes a component (that may be referred to as an "SCG-Z" component) shown generally at 268 in a "z" dimension or direction. The "z" dimension or direction may be a front-to-back or rostral-caudal dimension or direction relative to the subject, or a dimension or direction towards and away from the subject.

The example of FIG. 19 also includes a time series of GCG measurements of rotational velocity (or, more generally, rotational movement) shown generally at 269 around three axes of rotation. In the embodiment shown, the time series of GCG measurements of rotational movement 269 includes a component (that may be referred to as a "GCG-X" component) shown generally at 270 around an "x" axis of rotation. The "x" axis of rotation may be a left-to-right, side-to-side, or lateral-medial axis of rotation relative to the subject. In the embodiment shown, the time series of GCG measurements of rotational movement 269 also includes a component (that may be referred to as a "GCG-Y" component) shown generally at 272 around a "y" axis of rotation. The "y" axis of rotation may be a head-to-toe or superior-inferior axis of rotation relative to the subject. In the embodiment shown, the time series of GCG measurements of rotational movement 269 also includes a component (that may be referred to as a "GCG-Z" component) shown generally at 274 around a "z" axis of rotation. The "z" axis of rotation may be a front-to-back or rostral-caudal axis of rotation relative to the subject, or an axis of rotation extending towards and away from the subject.

In general, the time series of SCG and GCG measurements are time series of measurements of movement caused by the heart of the subject over a period of time. Further, in general, the time series of ECG measurements and the time series of measurements of movement are time series of measurements of electromechanical characteristics (or more generally of at least one characteristic) of the heart of the subject during a period of time. In general, such measurements may be synchronized, for example within about 4 ms or within about 5 ms of each other, or within 0 ms of each other. In the example of FIG. 19, the time series are measured over the same time periods, so that time periods of the time series are overlapping. More generally, such time series may be over periods of time that may be the same, or that may be different, and that may be overlapping in some embodiments.

As indicated above, in some embodiments, measuring both rotation (such as GCG measurements, for example) and linear movement (such as SCG, for example) may allow for increased opportunities for identifying time intervals or otherwise for analysis when compared to analyses that do not include measurements of both rotation and linear movement.

In summary, FIG. 19 illustrates electromechanical characteristics including time series of ECG, SCG, and GCG measurements of the heart of the subject. As indicated above, in some embodiments, measuring both rotation (such as GCG measurements, for example) and linear movement (such as SCG, for example) may allow for increased opportunities for identifying time intervals or otherwise for analysis when compared to analyses that do not include measurements of both rotation and linear movement.

However, FIG. 19 is an example only, and alternative embodiments may include measurements of more, fewer, and/or different characteristics of a heart of a subject. For example, as indicated above, some embodiments may include only a time series of ECG measurements and a time series of SCG-Z measurements because SCG-Z measurements may indicate particularly useful cardiac timing information, such as cardiac timing information regarding opening and closing of heart valves such as the aortic valve, for example. Nevertheless, other embodiments may include different combinations of time series of some or all of ECG, SCG-X, SCG-Y, SCG-Z, GCG-X, GCG-Y, and GCG-Z measurements, and other embodiments may include time series of still other measurements. In some embodiments, segmentation according to such time series of measurements of movement may involve segmentation according to a smooth absolute value of such time series of measurements of movement.

In general, a time series of ECG measurements may have identifiable waves known to a person skilled in the art. Such identifiable waves may include a "P" wave, a "Q" wave, and an "R" wave, for example. A "P" wave may represent atrial depolarization, which may result in atrial contraction or in atrial systole. A "Q" wave may be defined as any downward deflection after an immediately preceding "P" wave. An "R" wave may be defined by an upward deflection after an immediately preceding "Q" wave. An "S" wave may be defined as any downward deflection after the "R" wave, and a "T" wave may follow the "S" wave.

Referring to FIG. 18, in the embodiment shown, the codes at block 260 may cause the processor circuit 246 to segment the measurements indicated in the at least one measurement output signal received at block 258 in different ways. For example, the measurements may be segmented into cardiac cycles. Such segmentation may be referred to as "beat detection" and is shown at 275 in FIG. 15. In some embodiments, a cardiac cycle may be defined as a segment between adjacent "Q" waves (such as a segment between peaks of adjacent "Q" waves). In other embodiments, a cardiac cycle may be defined as a segment between adjacent "R" waves (such as a segment between peaks of adjacent "R" waves) or other corresponding defined portions in ECG measurements of adjacent cardiac cycles. In other words, defined portions of ECG measurements may be used for "beat detection" by identifying cardiac cycles.

In the embodiment of FIG. 19, segments shown generally at 276, 278, 280, 282, 284, 286, 288, 290, 292, 294, and 296 each represent one cardiac cycle between adjacent "Q" waves in the time series of ECG measurements 262. In the embodiment shown, all of the SCG and GCG time series are segmented into cardiac cycles between adjacent "Q" waves in the time series of ECG measurements 262. Therefore, in embodiments such as the embodiment shown, time series of measurements of movement caused by the heart of the subject may be segmented according to the time series of ECG measurements 262. However, segmentation in alternative embodiments may differ.

The measurements indicated in the at least one measurement output signal received at block 258 may also be segmented according to one or more of the cardiac cycles, such as one or more of the cardiac cycles defined between adjacent "Q" waves or one or more of the cardiac cycles defined between adjacent "R" waves, for example. Such segmentation is shown at 297 in FIG. 15.

Figure 20:
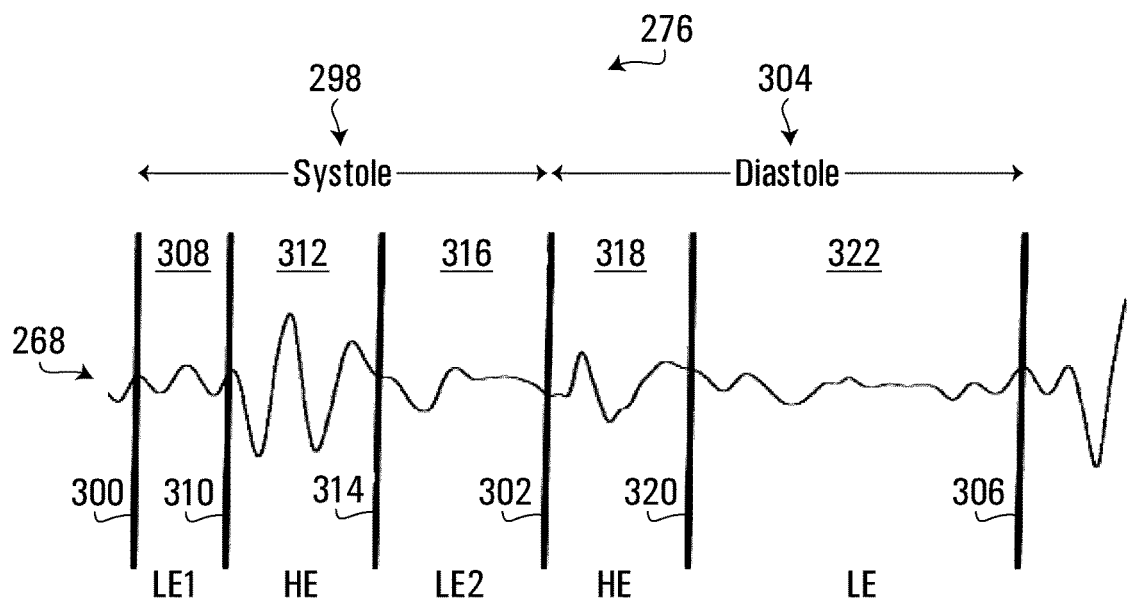
FIG. 20 illustrates segments of a time series of measurements of movement in a cardiac cycle in one embodiment.
Figure 21:
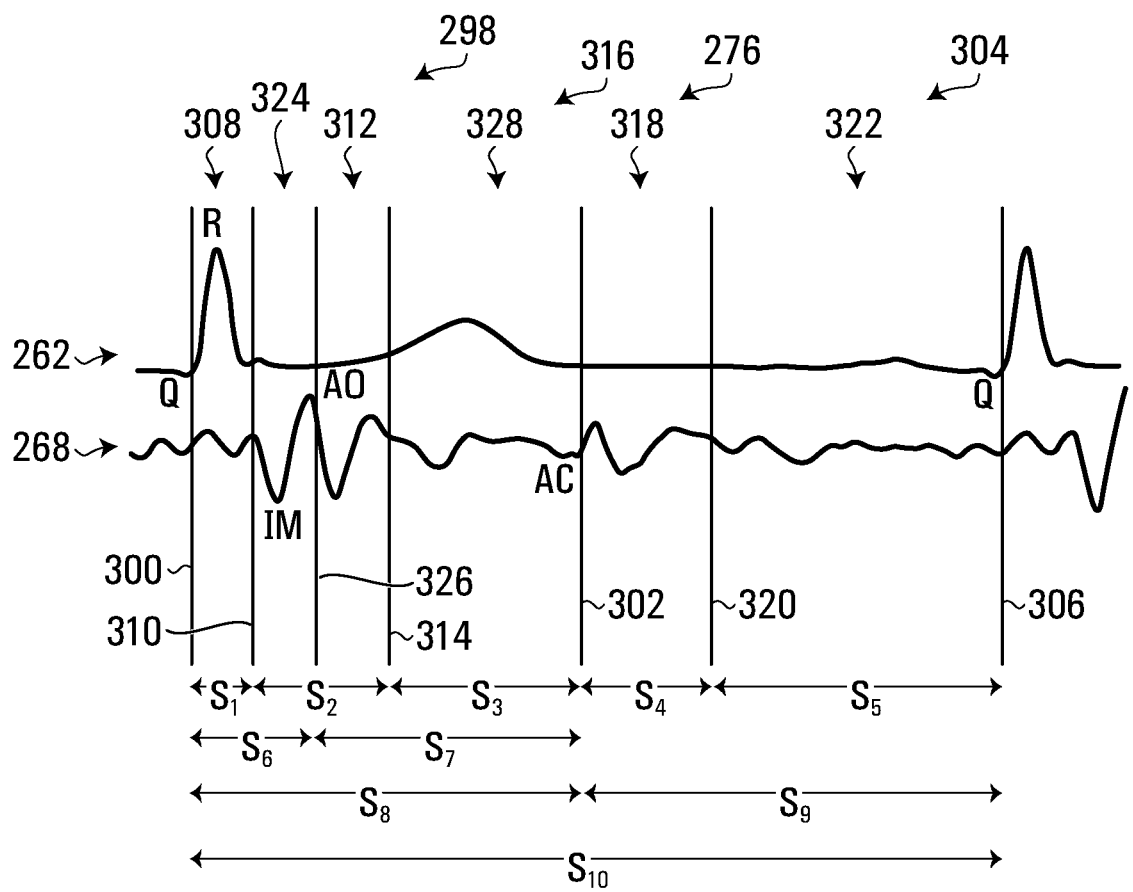
FIG. 21 illustrates segments of a time series of electrocardiogram ("ECG") measurements in the cardiac cycle of FIG. 20 in one embodiment, and segments of the time series of measurements of movement of FIG. 20.

For example, referring to FIGS. 15, 20, and 21, the time series of SCG-Z measurements 268 in the segment 276 (or "$S_{10}$") may be further segmented into:

1. a systole (or "$S_8$") segment shown generally at 298 and defined as between
   a. a "Q" wave 300 of the time series of ECG measurements 262 and
   b. an immediately subsequent aortic closure (or "AC") or an immediately subsequent start of diastolic vibration 302 (which may be defined as high-energy vibration due to aortic valve closure) identified in the time series of SCG-Z measurements 268 (or more generally in a time series of measurements of movement, for example from a derivative of GCG-X and GCG-Y); and 2. a diastole (or "$S_9$") segment shown generally at 304 and defined as between
    a. the AC or start of diastolic vibration 302 and
    b. an immediately subsequent "Q" wave 306 of the time series of ECG measurements 262.

In general, such systole (or "$S_8$") and diastole (or "$S_9$") segments may be considered main segments of a cardiac cycle.

The systole segment 298 may be further segmented into:
1. a first low-energy systole (or "LE1" or "$S_1$") segment shown generally at 308 and defined as between
    a. the "Q" wave 300 and
    b. an immediately subsequent start of systolic vibration 310 identified in the time series of SCG-Z measurements 268 (or more generally in a time series of measurements of movement);
2. a high-energy systole (or "HE" or "$S_2$") segment shown generally at 312 and defined as between
    a. the start of systolic vibration 310 and
    b. an immediately subsequent end of systolic vibration 314 identified in the time series of SCG-Z measurements 268 (or more generally in a time series of measurements of movement); and
3. a second low-energy systole (or "LE2" or "$S_3$") segment shown generally at 316 and defined as between
    a. the end of systolic vibration 314 and
    b. the AC or start of diastolic vibration 302.

In some embodiments, the start of systolic vibration 310 may be identified by mitral valve closure ("MC") in the time series of SCG-Z measurements 268 (or more generally in a time series of measurements of movement), and MC may identified by a peak immediately preceding isovolumic movement ("IM") as shown in FIG. 21. In some embodiments, MC has cycle-to-cycle consistency, which may facilitate segmentation as described herein, for example. However, in other embodiments, the start of systolic vibration 310, and thus the LE1 (or $S_1$) segment 308 and the HE systole (or $S_2$) segment 312, may be identified in other ways.

The "Q" wave 300 may indicate ECG depolarization and may indicate a start of electrical systole, whereas the start of systolic vibration 310 may indicate a start of mechanical systole. Therefore, the LE1 (or $S_1$) segment 308 may indicate electromechanical delay from the start of electrical systole to the start of mechanical systole, and in other embodiments, the LE1 (or $S_1$) segment 308 may be defined in other ways that define the same or similar electromechanical delay, for example.

Further, the HE systole (or $S_2$) segment 312 may capture a main interval of contraction, which may be approximately during isovolumetric contraction and rapid ejection. Therefore, in other embodiments, the HE systole (or $S_2$) segment 312 may be defined in other ways that define the same or similar isovolumetric contraction and rapid ejection, for example.

In general, the HE systole (or $S_2$) 312 segment may represent a rapid ejection systole phase of heart contraction, and the LE2 (or $S_3$) segment 316 may represent an immediately subsequent reduced ejection systole phase of heart contraction. Those phases may be segmented according to the time series of SCG-Z measurements 268 (or more generally according a time series of measurements of movement) as described herein, for example. Further, in other embodiments, the HE systole (or $S_2$) segment 312 and the LE2 (or $S_3$) segment 316 may be defined in other ways that define the same or similar rapid and reduced ejection systole phases, for example.

Further, the diastole segment 304 may be further segmented into:
1. a high-energy diastole (or "HE" or "$S_4$") segment shown generally at 318 and defined as between
    a. the AC or start of diastolic vibration 302 and
    b. an immediately subsequent end of diastolic vibration 320 identified in the time series of SCG-Z measurements 268 (or more generally in a time series of measurements of movement); and
2. a low-energy diastole (or "LE" or "$S_5$") segment shown generally at 322 and defined as between
    a. the end of diastolic vibration 320 and
    b. the "Q" wave 306.

In general, the HE diastole (or $S_4$) segment 318 may represent a rapid diastole phase of heart filling, and the LE (or $S_5$) segment 322 may represent an immediately subsequent reduced diastole phase of heart filling. Those phases may be segmented according to the time series of SCG-Z measurements 268 (or more generally according to a time series of measurements of movement) as described herein, for example. Therefore, in other embodiments, the HE diastole (or $S_4$) segment 318 and the LE (or $S_5$) segment 322 may be defined in other ways that define the same or similar rapid and reduced diastole heart filling phases, for example.

Further, the time series of SCG-Z measurements 268 in the segment 276 may be further segmented into:
1. a pre-ejection period (or "PEP" or "$S_6$") segment shown generally at 324 and defined as between
    a. the "Q" wave 300 and
    b. an immediately subsequent aortic opening ("AO") 326 identified in the time series of SCG-Z measurements 268 (or more generally in a time series of measurements of movement, for example from a derivative of GCG-X and GCG-Y); and
2. a left ventricle ejection time (or "LVET" or "$S_7$") segment shown generally at 328 and defined as between
    a. the AO 326 and
    b. the AC or start of diastolic vibration 302.

More generally, the PEP (or $S_6$) segment 324 may be defined as systolic time before rapid ejection when blood is ejected from the heart to the rest of the body, and may be defined to include an isovolumetric contraction period and electromechanical delay as described above. The PEP (or $S_6$) segment 324 may also be defined as a segment that ends when pressure in a ventricle is relatively high. Therefore, in other embodiments, the PEP (or $S_6$) segment 324 may be defined in other ways such as those described above, for example.

Further, more generally, the LVET (or $S_7$) segment 328 may be defined as a time period when blood is ejected from the aortic valve of the heart to the rest of body, and may be defined to include a rapid ejection period followed by a reduced ejection period. Therefore, in other embodiments, the LVET (or $S_7$) segment 328 may be defined in other ways such as those described above, for example.

More generally, in alternative embodiments, such segments may be defined alternatively. For example, the end of an ECG "T" wave or a "dub" heart sound may roughly approximate AC. Therefore, intervals defined above according to AC could alternatively be defined by an end of an ECG "T" wave or a "dub" heart sound, for example.

As indicated above, in some embodiments, measuring both rotation (such as GCG measurements, for example) and linear movement (such as SCG, for example) may allow for increased opportunities for identifying time intervals or otherwise for analysis when compared to analyses that do not include measurements of both rotation and linear movement, and the segments as defined above are examples of segments that may be more easily identified from measuring both rotation and linear movement, or that may be identified only from measuring both rotation and linear movement. In other words, measurements of both rotation and linear movement may provide different perspectives that may be combined to identify segments that may not be identifiable, reliably or at all, from only measurements of rotation or from only measurements of linear movement.

In general, in embodiments such as those described herein for example, segments in time series of measurements may be identified from the measurements themselves, or from other measurements. For example, some segments may be identified from a point in time identified in a time series of ECG measurements and from a point in time identified in a time series of measurements of movement.

The segments as defined above are examples only. Different embodiments may include one, some, or all of the segments as defined above and/or other segments. Further, some embodiments may omit segmentation and may thus omit blocks 260, 297, and 330.

Referring back to FIG. 18, after block 260, the program codes in the program memory 250 may continue at block 330, which includes codes for directing the microprocessor 248 to store the segmented measurements (as received at 258 and as segmented at block 260) in the storage memory 252 (shown in FIG. 17).

After block 330, the program codes in the program memory 250 may continue at block 332, which includes codes for directing the microprocessor 248 to identify one or more physiological parameters from the measurements indicated in the at least one measurement output signal received at block 258. In general, such physiological parameters may include one or more timing parameters, one or more rhythm parameters, and/or one or more force parameters.

In the embodiment shown, the timing parameters may include:

1. heart rate, which may be defined as a number of "Q" waves or a number of "R" waves per unit of time in the time series of ECG measurements 262;
2. timing intervals such as durations of
  a. the PEP or $S_6$ segment 324,
  b. the LVET or $S_7$ segment 328,
  c. the systole or $S_8$ segment 298, and/or
  d. the diastole or $S_9$ segment 304;
3. systolic/diastolic coupling (as described below); and/or
4. peak twist/untwist rotational velocity interval (as described below).

During heart rotation, potential energy may be preserved and/or converted to kinetic energy, and as a result, systolic rotation may help diastolic rotation and diastolic rotation may help systolic rotation. In other words, systolic energy (which may be caused by rotation during contraction) may cause a proportional diastolic rotation. A change in a ratio between systolic and diastolic rotation, at rest and/or during exercise, may indicate cardiac abnormalities. Therefore, the systolic/diastolic coupling parameter identified above may be a ratio of systolic rotation speed to diastolic rotation speed, or a ratio of systolic rotation energy to diastolic rotation energy, for example. Systolic rotation speed or energy and diastolic rotation speed or energy could be calculated from systolic and diastolic segments of the time series of GCG measurements of rotational movement 269.

Also, in general, a contraction force in a heart may be generated by rotation of the heart, and such rotation in an apical region of the heart is generally in an opposite direction from such rotation in a base of the heart. Such opposite directions of rotation may cause twist of the heart, and a velocity of such twist may be identified from a difference between filtered gradients of rotational velocity measured (by gyroscopes, for example) at different locations, such as apical and base locations, for example. In some embodiments, using more than one gyroscope may improve measurement accuracy for both apical and base rotational twists. Such a twist velocity may reach one maximum during systole and one maximum during diastole, and the peak twist/untwist rotational velocity interval may be defined as a time interval between a time of maximum twist velocity during systole and a time of maximum twist velocity during diastole. Further, in the embodiment shown, the rhythm parameters may include:

1. heart rate variability, which may for example reflect variability of heart rate for a period of time, for example at least 5 minutes; and/or
2. variability of timing intervals, which may include analyses similar to analyses of heart rate variability but instead analyze variability of durations of intervals such as
  a. the PEP or $S_6$ segment 324,
  b. the LVET or $S_7$ segment 328,
  c. the systole or $S_8$ segment 298, and/or
  d. the diastole or $S_9$ segment 304.

Such analysis of variability of timing intervals may indicate efficiency of the contraction and resting periods.

Further, in the embodiment shown, the force parameters may include:

1. cardiac output, which may be measured as a volume of blood pumped during a period of time, such as one minute for example, which may be estimated from a nonlinear regression model based on SCG and GCG signals; and/or
2. peak magnitude of rotational heart velocity at the time of a peak twist/untwist interval as described above.

After block 332, the program codes in the program memory 250 may continue at block 334, which includes codes for directing the microprocessor 248 to store the physiological parameters that were identified at block 332 in the storage memory 252 (shown in FIG. 17).

After block 334, the program codes in the program memory 250 may continue at block 336, which includes codes for directing the microprocessor 248 to apply one or more screening models to measurements (such as the measurements received at 258, for example). Such screening models may reflect factors such as age of the subject, gender of the subject, body-mass index ("BMI") of the subject, and/or previous cardiac and/or other health conditions of the subject. In general, as indicated above, the screening test 244 and the screening models of block 336 may involve screening a subject for one or more cardiac abnormalities and may involve inferring that general cardiac function is either normal (in-range) or abnormal (out-of-range).

In some embodiments, the screening test 244 and the screening models of block 336 may involve determining whether the physiological parameters that were identified at block 332 are within respective ranges associated with normal general cardiac function, or whether one or more of the physiological parameters that were identified at block 332 are outside of respective ranges associated with normal general cardiac function. If one or more of the physiological parameters that were identified at block 332 are outside of respective ranges associated with normal general cardiac function, then the screening test 244 and the screening models of block 336 may infer that general cardiac function is abnormal. However, alternative embodiments may differ. Further, one or more of the physiological parameters that were identified at block 332 being outside of respective ranges associated with normal general cardiac function does not necessarily indicate cardiac disease, but could rather indicate onset of cardiac disease or could otherwise indicate that seeking professional medical attention may be prudent.

In some embodiments, such as in the method 240 for example, the screening test 244 may be an initial test. However, alternative embodiments may differ by involving a screening test (as described herein, for example) as part of a different method, and not necessarily as an initial test, or some embodiments may omit such a screening test.

In general, the functionality or screening test may screen for conditions that may be associated with abnormal cardiac function using parameters such as the physiological parameters from block 332 and stored in the storage memory 252 at block 334, which may relate generally to overall work and/or functionality of a heart. In some embodiments, a combination of parameters including cardiac time interval (and its variability), rotational twist/untwist velocity, coupling time, and cardiac output may be particularly effective. The screening models of block 336 may be referred to as "direct" models because the screening models of block 336 analyze physiological parameters such as those described above. However, screening models of other embodiments may differ.

In general, the screening test 244 may be used to screen individuals for abnormalities outside clinical settings, and may be used to monitor cardiac performance periodically, such as weekly, for example. In some embodiments, the screening test may infer that general cardiac function of a heart of a subject is abnormal when the heart is not working and/or functioning correctly, even where the subject does not necessarily have any cardiac disease. In some embodiments, such an inference that the heart is not working and/or functioning correctly may indicate possible onset of one or more cardiac diseases, so the screening test 244 may prevent cardiac disease. In general, the subject should seek medical advice very promptly when the screening test infers that general cardiac function is abnormal.

As shown in FIG. 16, if the screening test 244 inferred one or more probable cardiac abnormalities, then the method 242 may continue at one or more causation models as shown at 338, which may generally infer one or more possible or suggested general causes of one or more cardiac abnormalities. Therefore, after block 336, the program codes in the program memory 250 may continue at block 340, which includes codes for directing the microprocessor 248 to determine whether the one or more inferences from the one or more screening models at block 336 inferred one or more probable cardiac abnormalities.

If at block 340 the one or more inferences from the one or more screening models at block 336 inferred one or more probable cardiac abnormalities, then the program codes in the program memory 250 may continue at block 342, which includes codes for directing the microprocessor 248 to apply causation models to the physiological parameters from block 332 and stored in the storage memory 252 at block 334 to infer one or more possible or suggested general causes of one or more cardiac abnormalities from such physiological parameters.

In general, the one or more causation models at block 342 may infer whether the one or more probable cardiac abnormalities inferred at block 336 may be due to issues with timing, rhythm, and/or force of the heart of the subject. In some embodiments, abnormal timing may be associated with abnormal timing events, such as those described above for example. Also, in some embodiments, abnormal rhythm may be associated with atrial fibrillation or with a change in a normal rhythm (or arrhythmia) of the cardiac cycle. Also, in some embodiments, abnormal force may be associated with parameters related to the amount of work required for the heart to pump blood in each cardiac cycle. In some embodiments, one, more than one, or all of the aforementioned timing parameters, rhythm parameters, and/or force parameters may be compared to respective thresholds or other respective criteria. For example, abnormal timing may be identified if one or more timing parameters such as those described above are more or less than respective thresholds. As another example, abnormal rhythm may be identified if one or more rhythm parameters such as those described above are more or less than respective thresholds. As another example, abnormal force may be identified if one or more force parameters such as those described above are more or less than respective thresholds.

In general, such thresholds or other criteria may be identified by comparing timing parameters, rhythm parameters, and/or force parameters such as those described above from different populations of individuals, such as a population of individuals known to have no heart conditions, a population of individuals known to have arrhythmia, a population of individuals known to have coronary artery disease, and/or one or more populations of individuals known to have one or more other types of heart conditions or diseases. In view of such populations, a person skilled in the art may, for example, identify such thresholds or other criteria as a minimum threshold or as a maximum threshold that reflects a desired balance of accuracy, specificity, and sensitivity. Examples of how accuracy, specificity, and sensitivity may be estimated in some embodiments are discussed in further detail below in the context of CAD detection study #2.

After block 342, the program codes in the program memory 250 may continue at block 344, which includes codes for directing the microprocessor 248 to cause the network signal interface 256 to transmit at least one inference output signal (such as the at least one inference indication signal 180 as described above, for example) indicating at least one inference from the one or more screening models as applied at block 336 and/or at least one inference from the causation models as applied at block 342. After block 344, the program codes in the program memory 250 may end.

In general, the one or more causation models 338 may be used either for self-monitoring for different types of cardiac abnormalities, or in settings where individuals may be screened before going to a cardiologist or other medical professional. For example, if a subject feels one or more symptoms, such as chest pain for example, then a general practitioner might cause one or more sensor apparatuses (such as one or more of the sensor apparatus 102, 182, 188, 196, or 206 as described above, for example) to measure electromechanical characteristics of a heart of the subject (as described herein, for example), and might cause one or more computing devices to apply the one or more causation models 338 (as described herein, for example). At least one inference output signal (produced at block 344, for example) may suggest referring the subject to cardiologist for further examination and diagnosis. Therefore, the screening test 244 and the one or more causation models 338 may be used independently in some embodiments.

As shown in FIG. 16, after the screening test 244, if the screening test 244 did not infer any probable cardiac abnormalities, then the method 242 may continue at one or more specific models (or disease-specific models) in a specific test (or a disease-specific test) as shown at 345, which may infer one or more specific cardiac diseases (such as CAD, AFib, valvular stenosis (such as aortic valvular stenosis or other valvular disease), cardiomyopathy (such as hypertrophic obstructive cardiomyopathy, for example), and/or heart failure, for example).

In some embodiments, the one or more specific models may be associated with respective cardiac diseases. For example, in some embodiments, specific models of the specific test 345 may include a specific model associated with CAD, another specific model associated with AFib, another specific model associated with valvular stenosis (such as aortic valvular stenosis or other valvular disease), another specific model associated with cardiomyopathy (such as hypertrophic obstructive cardiomyopathy, for example), and/or another specific model associated with heart failure. Other embodiments may include more or fewer specific models that may be associated with one or more different respective cardiac diseases.

Therefore, if at block 340 the one or more inferences from the one or more screening models at block 336 did not infer any probable cardiac abnormalities, then the program codes in the program memory 250 may continue at block 346 for each of one or more specific models to be applied. For example, in an embodiment that applies only a specific model associated with AFib, the codes in the program memory 250 may continue at block 346 only once in respect of a specific model associated with AFib. In other embodiments, more than one specific model may be applied, and in such embodiments, the codes in the program memory 250 may continue at block 346 repeatedly in respect of each specific model that is applied.

Some heart conditions or diseases of a heart are asymptomatic when the heart is not stressed, but such heart conditions or diseases may cause symptoms when the heart is stressed. Therefore, in general, different specific models of the specific test 345 may be associated with one or more respective specific tests that may facilitate inferring a likelihood of the associated cardiac disease. For example, a specific model associated with CAD may be associated with one or more tests associated with CAD, and a specific model associated with cardiomyopathy may be associated with one or more tests associated with cardiomyopathy. Such tests may be the same or may be different. For example, a test associated with CAD may be the same as a test associated with cardiomyopathy, or a test associated with CAD may be different from a test associated with cardiomyopathy.

As one example of a test associated with a specific specific cardiac disease, CAD may be associated with a pre-stress test and with a post-stress test to increase heart rate. Such tests may have a duration of about two minutes, for example. As another example, a 24-hour data capture may be required in some cases.

Therefore, block 346 includes codes for directing the microprocessor 248 to cause the network signal interface 256 to transmit at least one testing description output signal to communicate to a user a test associated with the specific model that is being applied. The at least one testing description output signal transmitted at block 346 may cause the sensor apparatus 102, the local computing device 104, and/or one or more other devices to produce at least one output signal that may be visible, audible, and/or otherwise discernible to communicate to the user an identification of or other details related to the test associated with the specific model that is being applied. In general, embodiments disclosed herein may include a sensor apparatus or another computing device, such as one or more devices for personal monitoring, for example, that may suggest and/or prioritize one or more tests associated with one or more respective specific models that are being applied.

After block 346, the program codes in the program memory 250 may continue at block 348, which includes codes for directing the microprocessor 248 to cause the network signal interface 256 to receive at least one measurement output signal (which may be similar to the at least one measurement output signal 178 shown in FIG. 6, for example) representing time series of measurements from a test by one or more sensor apparatuses (such as the sensor apparatus 102, for example) in response to the at least one testing description output signal transmitted at block 346.

After block 348, the program codes in the program memory 250 may continue at block 350, which includes codes for directing the microprocessor 248 to segment the measurements indicated in the at least one measurement output signal received at block 348. The codes at block 350 may be similar to the codes at block 260 as described above. After block 350, the program codes in the program memory 250 may continue at block 352, which includes codes for directing the microprocessor 248 to store the segmented measurements (as received at 348 and as segmented at block 350) in the storage memory 252 (shown in FIG. 17).

After block 352, the program codes in the program memory 250 may continue at block 354, which includes codes for directing the microprocessor 248 to apply the specific model being applied to by analyzing the segmented measurements as segmented at block 350 and as stored in the storage memory 252 at block 352.

Such specific models may reflect factors such as age of the subject, gender of the subject, BMI of the subject, and/or previous cardiac and/or other health conditions of the subject. Further, in general, the one or more specific models of the specific test 345 may use a machine learning methodology to analyze vibration measurements (such as SCG measurements of linear acceleration and GCG measurements of rotational movement, or some or all of the components thereof, for example) to find a dissimilarity with a normal heart condition.

For example, complexity associated with specific morphology of vibration measurements may be used for classification of CAD.

As another example, statistics and/or time complexity associated with a segment of one or more vibration measurements that delimits atrial contraction (which may be identified as a segment between a "T" wave and an immediately subsequent "Q" wave in a time series of ECG measurements) may be important for detection of AFib.

As another example, a change in statistics and/or time complexity associated with a segment of one or more vibration measurements that relates to a particular valve may be important for detection of valvular disease such as valvular stenosis, for example.

As another example, a change in time complexity of one or more vibration measurements over an entire cardiac cycle may be important for detection of cardiomyopathy and/or heart failure.

As another example, a ratio of the duration of the PEP or $S_6$ segment 324 to the duration of the LVET or $S_7$ segment 328 (as described above, for example) may be inversely correlated with stroke volume ("SV"), and a low percentage of SV (such as SV less than or equal to about 35%, for example) may indicate heart failure.

In general, complexity of features associated with segments of vibration measurements (such as the segments described above, for example) over time and statistical (such as mean and/or variance, for example) measures of such segments of vibration measurements may be used in specific models to infer specific coronary diseases.

As shown at 355 in FIG. 15, features may be extracted from segments of vibration measurements such as the segments identified as $S_1$, $S_2$, $S_3$, $S_4$, $S_5$, $S_6$, $S_7$, $S_8$, $S_9$, and $S_{10}$ above and in FIGS. 15 and 21. Such extracted features are identified as an example only as $F_1$, $F_2$, $F_3$, $F_4$, $F_5$, $F_6$, $F_7$, $F_8$, $F_9$, and $F_{10}$ in FIG. 15, although alternative embodiments may have more or fewer features.

For example, for each type of cardiac disease, a probabilistic model may be designed in which extracted features may be mathematical parameters that may be derived from different segments of the vibration measurements, such as the segments described above, for example.

In general, features that may be extracted from segments of vibration measurements may include one or more time features, one or more frequency features, one or more nonlinear features, one or more features of time and frequency, and/or one or more nonlinear features of time and frequency.

Such features of time may include one or more of mean, standard, deviation, root mean square, mean of square, standard error of mean, skewness, kurtosis, mean absolute deviation, median top 10, median low 10, energy, and/or energy entropy.

Such features of frequency may include one or more of total power spectral density ("PSD"), maximum PSD location frequency, maximum PSD value frequency, spectral entropy, band power, bandwidth 3 db, mean frequency, median frequency, and/or total harmonic distortion.

Such nonlinear features may include one or more of sample entropy, maximum entropy, Shannon entropy, maximum Lyapunov, correlation dimension, recurrence quantification analysis (which may include one or more of recurrence rate, determinism, luminarity, ratio, average diagonal line length, trapping time, longest diagonal line, longest vertical line, divergence, Shannon entropy, and/or trend), Hurst exponent, and/or fractal dimension.

Such features of time and frequency may include one or more of ridge time from time frequency, ridge time from nonlinear frequency, ridge frequency from time frequency, and/or ridge frequency from nonlinear frequency.

Such nonlinear features of time and frequency may include one or more of wavelet entropy and/or multiscale entropy.

Further, as shown in FIG. 15, cross features may also be extracted from segments of vibration measurements. In general, such cross features may correspond to features associated with different segments of the same type of measurement of vibration or with different segments of different types of measurements of vibration. For example, a ratio of maximum amplitude in the systole ($S_9$) segment to maximum amplitude in the diastole ($S_8$) segment of SCG-Z measurements may be a cross feature associated with the same type of measurement of vibration. However, a ratio of maximum amplitude of SCG to a derivative of GCG is an example of a cross feature associated with two different types of measurements of vibration.

After such features and/or cross features have been extracted and/or calculated for one or more cardiac cycles, statistics and time complexity measures may be extracted for some or all of such features and/or cross features to reflect overall behavior of measurements for a particular test.

In some embodiments, such statistics may include mean, median, standard deviation, kurtosis, and/or other statistical measures, for example. Such statistics are identified as an example only as $ST_1$, $ST_2$, $ST_3$, $ST_4$, $ST_5$, $ST_6$, $ST_7$, $ST_8$, $ST_9$, and $ST_{10}$ in FIG. 15. Further, FIG. 15 illustrates statistical cross features, which may be identified similarly to cross features as described above, for example. However, alternative embodiments may have more or fewer statistics and may or may not include statistical cross features.

In some embodiments, time complexity features as described above may illustrate, in some sense, a measure of unpredictability of the features over a period of time. Such time complexity features are identified as an example only as $TC_1$, $TC_2$, $TC_3$, $TC_4$, $TC_5$, $TC_6$, $TC_7$, $TC_8$, $TC_9$, and $TC_{10}$ in FIG. 15. Some features may show a level of complexity associated with part of a signal, whereas time complexity features may show the complexity over a fixed time. Further, FIG. 15 illustrates time complexity cross features, which may be identified similarly to cross features as described above, for example. However, alternative embodiments may have more or fewer time complexity features and may or may not include time complexity cross features.

The features as described above may be extracted from the segments of vibration measurements as described above, and such extracted features may quantify the complexity of the morphology for the different segments of the vibration measurements. In the specific models applied at block 354, the statistics and the time complexity features as described above could indicate whether a morphology of vibration measurements is consistent with a morphology associated with a normal heart, or whether the morphology of vibration measurements is consistent with one or more morphologies associated with a heart having a respective particular cardiac disease (such as CAD, for example).

The specific models applied at block 354 may be referred to as "indirect" models because the specific models applied at block 354 analyze features, cross features, statistics, statistical cross features, time complexity features, and/or time complexity cross features such as those described above. However, specific models of other embodiments may differ.

Some or all of the features, cross features, statistics, statistical cross features, time complexity features, and/or time complexity cross features may be factors in classification shown at 357 in FIG. 15. The classification may infer a probability of the cardiac disease associated with the specific model that is being applied. For example, as shown in FIG. 15, the probability may range from 0 to 1, and a probability from 0 to S may indicate that the cardiac disease associated with the specific model that is being applied is unlikely. Further, a probability from E to 1 may indicate that the cardiac disease associated with the specific model that is being applied is likely, and a probability from S to E may indicate that the model that is being applied is inconclusive.

Research has suggested that vibration characteristics (or morphology) of a heart may change differently when the heart has different types of cardiac disease. Therefore, although without wishing to be bound by any particular theory, embodiments such as those described herein may involve one or more models that may consider morphology of vibration measurements (such as SCG measurements of linear acceleration and GCG measurements of rotational movement, or some or all of the components thereof, for example) and variation of such vibration measurements over time for particular different cardiac diseases. Such models may be more accurate or more useful when compared to other analyses that may, for example, analyze measurements only for timing parameters or simply for one or more amplitudes.

Referring back to FIG. 18, after block 354, the program codes in the program memory 250 may continue at block 356, which includes codes for directing the microprocessor 248 to transmit at least one inference output signal (such as the at least one inference indication signal 180 as described above, for example) indicating at least one inference from the specific model applied at block 354. The at least one inference output signal transmitted at block 356 may cause the sensor apparatus 102, the local computing device 104, and/or one or more other devices to produce at least one output signal that may be visible, audible, and/or otherwise discernible to communicate to the user at least one inference the specific model applied at block 354. In general, the subject should seek medical advice very promptly when one or more of the specific models infers that the subject may have any cardiac disease.

As indicated above, the program codes in the program memory 250 may continue at block 346 for each of one or more specific models to be applied. Each time that the program codes in the program memory 250 continue at block 346, the program codes in the program memory 250 may continue at blocks 348, 350, 352, 354, and 356 as described above. Therefore, after block 356, if any further specific models remain to be applied, then the program codes in the program memory 250 may continue at block 346. Dashed lines around blocks 346, 348, 350, 352, 354, and 356 in FIG. 18 indicate blocks that may be repeated for each of one or more specific models to be applied.

As shown in FIG. 16, if the screening test 244 did not infer any probable cardiac abnormalities, and if the one or more specific models of the specific test 345 do not infer any probable cardiac diseases, then an exercise type may be identified (as shown at 358) for use in a cardiac fitness test as shown at 360. The exercise type may be a type of aerobic exercise or a type of anaerobic exercise, for example. Such an exercise type may be user-selected. For example, a user may select slow jogging. In some embodiments, such an exercise type may typically be an aerobic exercise.

Therefore, after the program codes in the program memory 250 have continued at blocks 346, 348, 350, 352, 354, and 356 for all of the specific models to be applied, the program codes in the program memory 250 may continue at block 361, which includes codes for directing the microprocessor 248 to determine whether the one or more specific models as applied at block 354 inferred that any specific cardiac disease is likely present.

If at block 361 the one or more specific models as applied at block 354 inferred that any specific cardiac disease is likely present, then the program codes in the program memory 250 may end. However, if at block 361 the one or more specific models as applied at block 354 did not infer that any specific cardiac disease is likely present, then the program memory 250 may continue at block 362, which includes codes for directing the microprocessor 248 to identify an exercise type for the cardiac fitness test 360.

After block 362, the program codes in the program memory 250 may continue at block 364, which includes codes for directing the microprocessor 248 to cause the network signal interface 256 to transmit at least one suggestion output signal indicating at least one suggestion of a fitness test to the local computing device 104. The at least one suggestion output signal transmitted at block 364 may cause the sensor apparatus 102, the local computing device 104, and/or one or more other devices to produce at least one output signal that may be visible, audible, and/or otherwise discernible to communicate to the user an identification of or other details related to the at least one suggestion of a fitness test.

After block 364, the program codes in the program memory 250 may continue at block 366, which includes codes for directing the microprocessor 248 to cause the network signal interface 256 to receive at least one measurement output signal (which may be similar to the at least one measurement output signal 178 shown in FIG. 6, for example) representing time series of measurements from a fitness test by one or more sensor apparatuses (such as the sensor apparatus 102, for example). In general, such measurements may include measurements such as those described herein before physical activity, during physical activity, and/or after physical activity as identified at block 362 and as indicated at block 364.

After block 366, the program codes in the program memory 250 may continue at block 368, which includes codes for directing the microprocessor 248 to identify a cardiac performance index ("CPI") from the least one measurement output signal received at block 366. In general, the CPI may indicate an estimation of cardiac fitness. Other estimates of cardiac fitness may involve a % VO$_2$Max test or a test of heart rate recovery. However, the CPI as described herein may be simpler or easier to obtain than a % VO$_2$Max test or a test of heart rate recovery, for example.

The CPI may be a number between 0 and 100, and may indicate an estimated cardiac fitness level of the subject. A subject could improve the CPI by training (for example endurance and/or strength exercise) over a training timeframe.

Such screening models may reflect factors such as age of the subject, gender of the subject, BMI of the subject, and/or previous cardiac and/or other health conditions of the subject. Further, the CPI may be determined by applying machine learning techniques to parameters and/or features that may include one or more of 1. drop of heart rate,
2. variability heart rate (as described above, for example),
3. variability (as described above, for example) cardiac time intervals (such as the segments described above, for example), and/or
4. maximum amplitude of contraction during systole.

In general, heart rate recovery after exercise may indicate cardiac fitness. However, several other cardiac parameters—including cardiac output, systolic contribution of the cardiac cycle, and peak of twisting/untwisting force produced during and after exercise—may provide a more accurate estimation of cardiac fitness.

Therefore, embodiments such as those described herein may analyze some or all of the following parameters:

1. heart rate recovery and/or variability (for example, heart rate immediately after exercise may be compared to heart rate two minutes (or a different period of time) after exercise, and a faster recovery or slowdown in heart rate may indicate a healthier heart); and/or
2. cardiac time interval recovery rate and/or variability (for example, one or more cardiac time intervals (such as the segments described above, for example) immediately after exercise may be compared to such one or more cardiac time intervals two minutes (or a different period of time) after exercise, and a faster recovery or slowdown in such one or more cardiac time intervals may indicate a healthier heart).

In some embodiments, the CPI may be a weighted average of extracted parameters such as those described above. Identification of relevant parameters and weights for relevant parameters may involve considering such parameters for individuals with different levels of cardiovascular fitness, and may involve using a regression model that may compare parameters such as those described above to metabolic measurements recommended by the American College of Sports Medicine. Such parameters may include oxygen uptake reserve (% $VO_2R$ or % $VO_2Max$) calculated from resting to different oxygen levels and may be used in high-performance fitness to measure cardiac fitness. Embodiments such as those described herein may be highly correlated to such parameters, and models according to embodiments such as those described herein may be trained based on different types of exercise (such as aerobic and/or endurance exercises, for example).

In general, models that correlate to parameters such as % $VO_2Max$ may be more comprehensive and/or more accurate than analyses that use only heart-rate-related parameters (such as variability and/or drop, for example). Embodiments such as those described herein have been verified using % $VO_2Max$, which is a standard for fitness evaluation. Therefore, the CPI, as described herein for example, may more accurately represent cardiac fitness when compared to other technologies, such as technologies involving a smartwatch for example, that only measure heart rate and/or heart rate variability parameters.

After block 368, the program codes in the program memory 250 may continue at block 370, which includes codes for directing the microprocessor 248 to cause the network signal interface 256 to transmit at least one indication of the cardiac performance index identified at block 370 to the local computing device 104. After block 344, the program codes in the program memory 250 may end.

As shown in FIG. 16, embodiments such as those described herein may follow a hierarchical procedure that may progress from the screening test 244 to the specific test 345 (which may infer one or more specific cardiac diseases), and then to the cardiac fitness test 360 in cases where the screening test 244 does not infer any probable cardiac abnormalities and the specific test 345 does not infer any probable cardiac diseases. In general, the screening test 244, the specific test 345, and the cardiac fitness test 360 may be the same or may include different types of physical activity and corresponding recording duration. Further, in cases where the screening test 244 does infer one or more probable cardiac abnormalities, then the one or more causation models 338 may generally infer one or more possible or suggested general causes of one or more cardiac abnormalities.

However, alternative embodiments may differ, and for example, alternative embodiments may involve only some or only one or more parts of methods and procedures such as those described herein. For example, as indicated above, the screening test 244 and the one or more causation models 338 may be used independently in some embodiments. Therefore, some embodiments may involve only the one or more causation models 338 and may or may not involve the screening test 244, whereas some embodiments may involve only the screening test 244 and may or may not involve the one or more causation models 338. As another example, some embodiments may involve only the specific test 345. Further, some embodiments may include only one specific model, such as a model associated with AFib, for example. As another example, some embodiments may not involve the cardiac fitness test 360. Still other embodiments may include combinations of and/or variations of embodiments such as those described herein, or may omit and/or vary some or all of embodiments such as those described herein.

C. Experimental Studies

In a repeatability study, it was shown that under the constant conditions, in which subjects were in a supine position with no previous stress or coffee consumption, measurements as described herein were substantially consistent within intervals of 5-10 minutes and of 24 hours.

In a reproducibility study, it was shown that the timing associated with mitral and aortic valve opening and closing extracted from fiducial points of SCG were substantially consistent with such points identified according to echocardiography, which is an accepted standard for identifying such points.

One study involved analysis of a dataset of ECG and SCG-Z measurements of subjects having CAD. Analysis of the dataset suggested that vibration morphology, in combination with timing, may indicate CAD in subjects. In that analysis, accuracy appeared to have improved when stress exercises were conducted. Another study indicated that accuracy of detection of AFib may be increased in embodiments such as those described herein when compared to analyses that analyze only ECG. Further clinical studies may improve models (such as those described herein, for example) for detection of CAD, AFib, and/or other cardiac diseases.

Another study involved analysis of recovery of heart rate and systolic time intervals after submaximal bicycle exercise in 14 healthy and young male subjects. Heart rate, heart rate variability, cardiac timing intervals (which, in this study, were PEP, isovolumetric contraction time, LVET, and a ratio of PEP/LVET) were measured immediately after exercise and at different times of recovery after exercise. Preliminary results suggested that most recovery responses started immediately after exercise to return toward the resting values, but that the rates of change varied for different subjects with different levels of cardiac fitness.

Figure 22:
FIG. 22 illustrates ECG and seismocardiogram ("SCG") measurements before and after exercise according to a case study.

Another study ("case study #1") involved a 52-year-old male with no known CAD. FIG. 22 illustrates ECG and SCG measurements before and after exercise according to case study #1. In FIG. 22, 372 illustrates pre-exercise ECG measurements when the subject was supine, 374 illustrates pre-exercise SCG measurements when the subject was supine and synchronized with the pre-exercise ECG measurements 372, 376 illustrates post-exercise ECG measurements, and 378 illustrates post-exercise SCG measurements synchronized with the post-exercise ECG measurements 376. ECG measurements all showed clear "P" and "T" waves and no evidence of ST depression or elevation both pre- and post-exercise. Accordingly, the ECG measurements did not indicate ischemia. In low-energy segments of the SCG measurements as described above, no spike or high-frequency vibration is observed pre- or post-exercise. Accordingly, SCG morphology for all intervals was considered normal. Further, in the segments as described above, the morphology of the SCG measurements does not change over multiple consecutive cycles, and the SCG measurements follow the same pattern, so cycle-to-cycle variation of complexity was not significant. A screening method as described above categorized the subject as normal, and features of a screening model as described above of the screening method were all in a normal range with a probability of 92%. In a specific model for CAD, pre- and post-exercise, mean and complexity features were all in a normal range for each of the $S_1$ to $S_{10}$ segments. A model (as described above with reference to block 368, for example) considered both pre- and post-exercise measurements and used the models for a particular range of heart rate and cardiac output with a fitness level of 72%.

Figure 23:
FIG. 23 illustrates ECG and SCG measurements before and after exercise according to a case study.

Another study ("case study #2") involved a 60-year-old female with no known CAD. FIG. 23 illustrates ECG and SCG measurements before and after exercise according to case study #2. In FIG. 23, 380 illustrates pre-exercise ECG measurements when the subject was supine, 382 illustrates pre-exercise SCG measurements when the subject was supine and synchronized with the pre-exercise ECG measurements 380, 384 illustrates post-exercise ECG measurements, and 386 illustrates post-exercise SCG measurements synchronized with the post-exercise ECG measurements 384. ECG measurement all showed clear "P" and "T" waves and no evidence of ST depression or elevation both pre- and post-exercise. Accordingly, the ECG measurements did not indicate ischemia. In low-energy segments of the SCG measurements as described above, no spike or high-frequency vibration is observed pre- or post-exercise. Accordingly, SCG morphology for all the intervals was considered normal. Further, in the segments as described above, the morphology of the SCG measurements does not change over multiple consecutive cycles, and the SCG measurements follow the same pattern, so cycle-to-cycle variation of complexity was not significant. A screening method as described above categorized the subject as normal, and features of a screening model as described above of the screening method were all in a normal range with a probability of 93%. In a specific model for CAD, pre- and post-exercise, mean and complexity features were all in the normal range for each of the $S_1$ to $S_{10}$ segments. A model (as described above with reference to block 368, for example) considered both pre- and post-exercise measurements and used the models for a particular range of heart rate and cardiac output with a fitness level of 65%.

Figure 24:
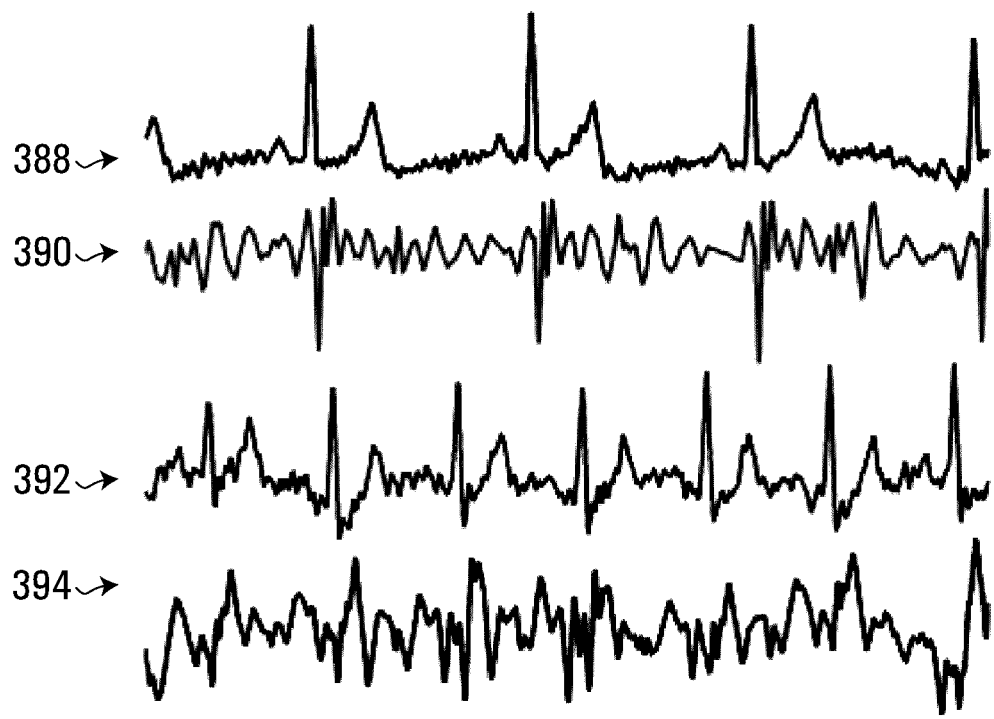
FIG. 24 illustrates ECG and SCG measurements before and after exercise according to a case study.

Another study ("case study #3") involved a 61-year-old male. Stent placement ("S/P") angioplasty and myocardial infarction had occurred two weeks prior. FIG. 24 illustrates ECG and SCG measurements before and after exercise according to case study #3. In FIG. 24, 388 illustrates pre-exercise ECG measurements when the subject was supine, 390 illustrates pre-exercise SCG measurements when the subject was supine and synchronized with the pre-exercise ECG measurements 388, 392 illustrates post-exercise ECG measurements, and 394 illustrates post-exercise SCG measurements synchronized with the post-exercise ECG measurements 392. The subject's left anterior descending and right coronary arteries were occluded more than 50%. ECG measurements showed no sign of pre-exercise ST elevation or depression, but did show post-exercise ST depression. Pre-exercise SCG measurement morphology was normal, but post-exercise SCG measurement morphology was inconsistent with normal SCG for all the $S_1$ to $S_{10}$ segments. For example, post-exercise, the HE and LE diastole segments $S_4$ and $S_5$ had the same energy level. Energy patterns and regularity (as shown in FIG. 20, for example) were not observed post-exercise. A post-exercise level of time complexity was significant with considerable cycle-to-cycle variation in the complexity measure. A screening method as described above assigned an abnormality probability of 80%. A causation model as described above showed problems associated with force of contraction in diastole and systole. A CAD specific model as described above assigned a probability of 93% based on pre- and post-exercise. However, without post-exercise measurements, the probability of CAD could not have been inferred. Specific models associated with AFib, stenosis, and cardiomyopathy showed a probability of less than 40%, which is insignificant. For example, in a specific model associated with AFib, energy associated with atrial contraction during a P-Q interval of vibration measurements (namely the LE or $S_5$ segment 322 shown in FIG. 21) showed an irregular pattern but not at a very high level, and such an irregular pattern may indicate AFib.

Figure 25:
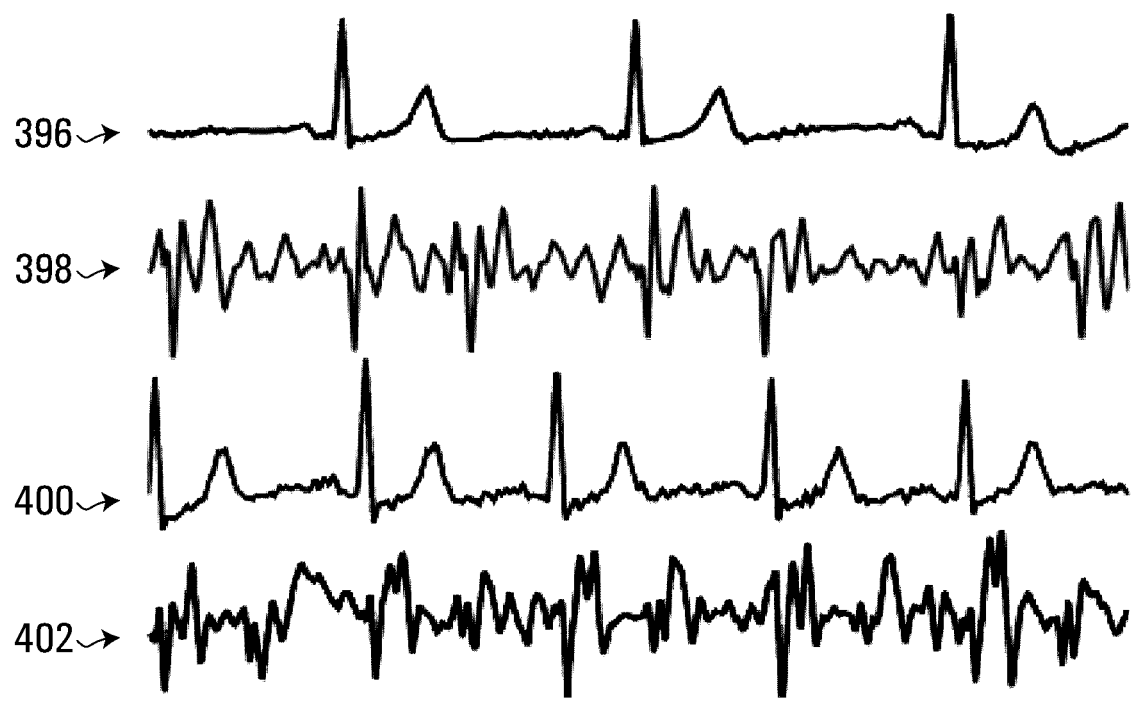
FIG. 25 illustrates ECG and SCG measurements before and after exercise according to a case study.

Another study ("case study #4") involved a 71-year-old female with medical management. FIG. 25 illustrates ECG and SCG measurements before and after exercise according to case study #4. In FIG. 25, 396 illustrates pre-exercise ECG measurements when the subject was supine, 398 illustrates pre-exercise SCG measurements when the subject was supine and synchronized with the pre-exercise ECG measurements 396, 400 illustrates post-exercise ECG measurements, and 402 illustrates post-exercise SCG measurements synchronized with the post-exercise ECG measurements 400. Myocardial infarction had occurred two weeks prior. The subject's left anterior descending and right coronary arteries were occluded more than 50%. ECG measurements showed no sign of pre-exercise ST elevation or depression, but did show post-exercise ST depression. Pre-exercise, SCG measurement morphology was consistent with normal SCG for all the $S_1$ to $S_{10}$ segments, except for a slight change in the $S_5$ segment. Post-exercise, SCG measurement morphology was inconsistent with normal SCG for all the $S_1$ to $S_{10}$ segments. For example, vibration periods were irregular, and the LE2 or $S_3$ segment had abnormally high energy. Further, a post-exercise level of time complexity was significant with considerable cycle-to-cycle variations in the complexity measure. A screening method as described above assigned an abnormality probability of 84%. A causation model as described above showed problems associated with force. A CAD specific model as described above assigned a probability of 95% based on pre- and post-exercise. Specific models associated with AFib, stenosis, heart failure, and cardiomyopathy showed a probability of less than 35%, which is insignificant.

Figure 26:
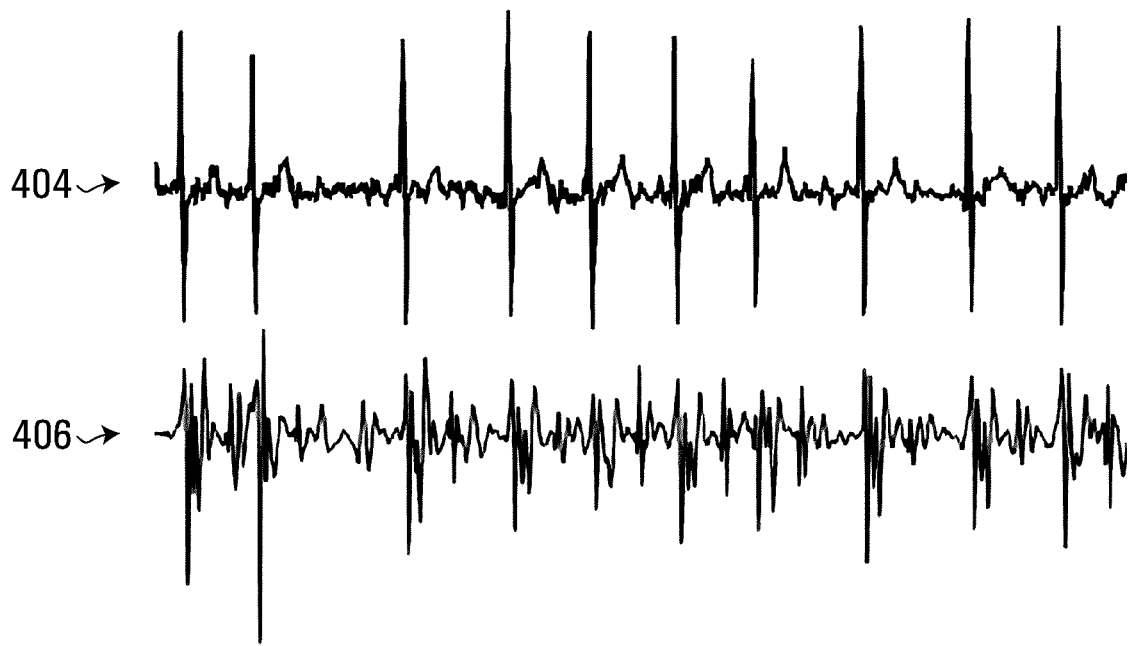
FIG. 26 illustrates ECG and SCG measurements during rest according to a case study.

Another study ("case study #5") involved a 60-year-old male with atrial fibrillation. FIG. 26 illustrates ECG and SCG measurements according to case study #5. In FIG. 26, 404 illustrates ECG measurements during rest, and 406 illustrates SCG measurements during rest and synchronized with the ECG measurements 404. The subject had no ECG "P" wave and had an irregular heart rhythm, which may in general indicate AFib. Further, cycle-to-cycle variation was abnormal in both ECG and SCG measurements. For example, the second cardiac cycle in FIG. 26 indicates an irregular pattern in diastolic atrial vibration, which also may in general indicate AFib. A screening method as described above assigned an abnormality probability of 92%. A causation model as described above showed causation associated with rhythm. An AFib specific model assigned a probability of 95% for the presence of AFib. Specific models associated with CAD, valvular stenosis, heart failure, and cardiomyopathy assigned a probability of less than 42%.

A CAD detection study ("CAD detection study #1") involved 204 subjects. Of those subjects, 164 had a coronary angiogram within six months either before or after an exercise stress test, and another 40 others had no more than a 2% estimated risk of coronary diseases. Among the 204 subjects, 130 were diagnosed with coronary diseases and 74 were considered as normal. The criterion for CAD was more than 50% occlusion in at least one coronary artery. A treadmill exercise stress test following the Bruce protocol was used to determine the effects of exercise on the heart of the subjects. SCG-Z and ECG measurements were obtained simultaneously in supine positions for about one minute immediately prior to the exercise test to establish a baseline, immediately after returning to supine positions at the end of the exercise, and after a five-minute recovery period after the exercise. The overall accuracy, sensitivity, and specificity values were estimated at 0.84, 0.85, and 0.83, respectively.

Another study ("CAD detection study #2") included measurements from 286 subjects. As with CAD detection study #1, SCG-Z and ECG measurements were obtained simultaneously with the subjects in supine positions. Of the 286 subjects of CAD detection study #2, 185 had CAD (defined in CAD detection study #2 as occlusion of more than 50% in at least one coronary artery according to a coronary angiogram within six months either before or after the measurements) and the remaining 101 were diagnosed as healthy.

The subjects of CAD detection study #2 were randomly assigned into either a training group (including about 75% of the subjects) or a test group (including about 25% of the subjects). The measurements from the subjects in the training group were used for feature selection and for training a probabilistic model (the "CAD classifier") to infer a likelihood of CAD. The measurements from the subjects in the test group were used to test (or validate) the trained CAD classifier. The CAD classifier is thus an example of a model associated with CAD.

Figure 27:
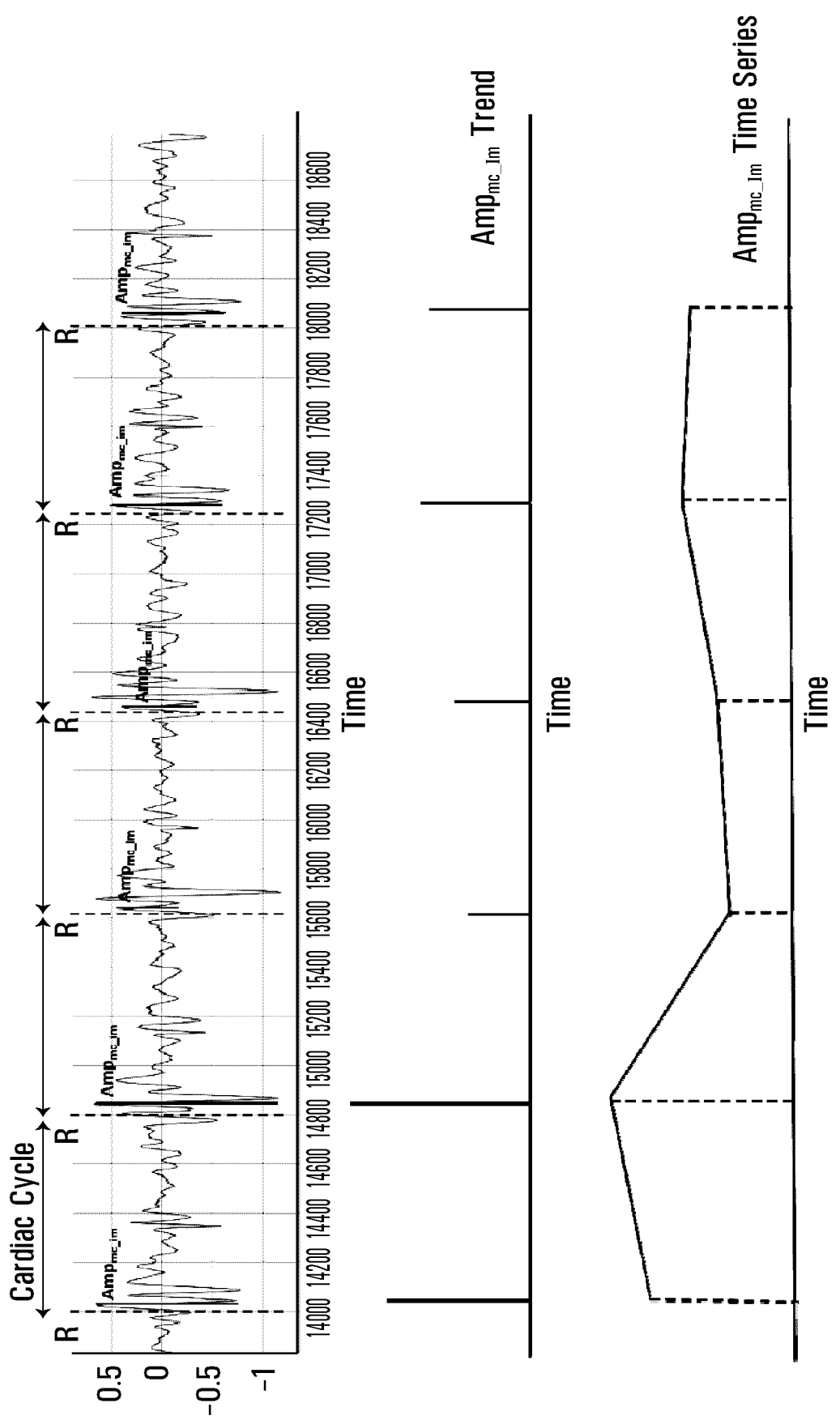
FIG. 27 illustrates examples of cardiac-cycle segments, examples of amplitudes of movement during MC-IM segments, and an example of a time series of amplitudes of movement during MC-IM segments according to a detection study.

In CAD detection study #2, ECG "R" peaks were used to segment time series of SCG measurements for each subject in the training group into cardiac cycles. As indicated above, FIG. 19 illustrates examples of such cardiac-cycle segments, and FIG. 27 illustrates examples of such cardiac-cycle segments in CAD detection study #2. In such cardiac-cycle segments of the time series of SCG measurements, fiducial points such as MC, IM, and AO (as described above) were identified, and then amplitudes of movement during MC-IM segments ($amp_{mc\text{-}im}$) between MC and IM fiducial points of the same cardiac-cycle segments, amplitudes of movement during IM-AO segments ($amp_{im\text{-}ao}$) between IM and AO fiducial points of the same cardiac-cycle segments, and ratios of $amp_{im\text{-}ao}/amp_{mc\text{-}im}$ were estimated. In CAD detection study #2, $amp_{mc\text{-}im}$, $amp_{im\text{-}ao}$, and $amp_{im\text{-}ao}/amp_{mc\text{-}im}$ were resampled evenly four times per second to produce a time series of $amp_{mc\text{-}im}$, a time series of $amp_{im\text{-}ao}$, and a time series of $amp_{im\text{-}ao}/amp_{mc\text{-}im}$. FIG. 27 also illustrates examples of $amp_{mc\text{-}im}$ in respective cardiac-cycle segments, and an example of a time series of $amp_{mc\text{-}im}$.

Then, the cardiac-cycle segments of the time series of SCG measurements for each subject in the training group were further segmented into the segments $S_1$, $S_2$, $S_3$, $S_4$, $S_5$, $S_6$, $S_7$, $S_8$, $S_9$, and $S_{10}$ as described above and as shown in FIG. 21. For each of the segments $S_1$, $S_2$, $S_3$, $S_4$, $S_5$, $S_6$, $S_7$, $S_8$, $S_9$, and $S_{10}$, a mean amplitude, standard deviation of amplitude, and power were estimated and were also resampled evenly four times per second to produce a time series of mean amplitude, a time series of standard deviation of amplitude, and a time series of power for each of the segments $S_1$, $S_2$, $S_3$, $S_4$, $S_5$, $S_6$, $S_7$, $S_8$, $S_9$, and $S_{10}$.

In summary, a total of 33 time series were produced from the measurements for each subject in the training group, namely a time series of $amp_{mc\text{-}im}$, a time series of $amp_{im\text{-}ao}$, a time series of $amp_{im\text{-}ao}/amp_{mc\text{-}im}$, and a time series of mean amplitude, a time series of standard deviation of amplitude, and a time series of power for each of the ten segments $S_1$, $S_2$, $S_3$, $S_4$, $S_5$, $S_6$, $S_7$, $S_8$, $S_9$, and $S_{10}$.

Then, the following 14 features were extracted from each of the 33 time series, so that 462 features were extracted from the measurements for each subject in the training group:

1. temporal features, namely
   a. mean,
   b. standard deviation,
   c. root mean square,
   d. power,
   e. skewness, and
   f. kurtosis;
2. spectral features, namely
   a. the total power of PSD and
   b. the maximum frequency of PSD; and
3. non-linear features, namely
   a. correlation dimension,
   b. sample entropy,
   c. approximate entropy,
   d. wavelet entropy,
   e. percentage of recurrence points in the recurrence plot ("REC"), and
   f. ratio of percentage of recurrence points that form diagonal lines ("DET") and REC.

Then, features extracted from the measurements for subjects in the training group were selected using univariate study. To do so, relationships between each of the extracted features and the presence of CAD in the training group were assessed by comparing median values of the extracted features in subjects in the training group with CAD to median values of the extracted features in subjects in the training group without CAD. In addition, univariate logistic regression was used to estimate area under the curve ("AUC") for each extracted feature. In CAD detection study #2, the extracted features that were selected for model development of the CAD classifier were the features having median values that were significantly different in subjects with and without CAD (p-value <=0.001) or having an AUC more than 0.75.

In CAD detection study #2, feature selection as described above resulted in selection of the following 17 extracted features.

| Feature | Name | Segment | Time Series | Feature |
|---|---|---|---|---|
| 1 | s1.mean.std | $S_1$ | mean | std |
| 2 | s4.std.mean | $S_4$ | std | mean |
| 3 | s4.std.RMS | $S_4$ | std | RMS |
| 4 | s4.std.power | $S_4$ | std | power |
| 5 | s4.std.wavelet.entropy | $S_4$ | std | wavelet.entropy |
| 6 | s4.power.mean | $S_4$ | power | mean |
| 7 | s4.power.RMS | $S_4$ | power | RMS |
| 8 | s4.power.power | $S_4$ | power | power |
| 9 | s7.mean.mean | $S_7$ | mean | mean |
| 10 | s7.mean.RMS | $S_7$ | mean | RMS |
| 11 | s7.mean.power | $S_7$ | mean | power |
| 12 | s8.mean.mean | $S_8$ | mean | mean |
| 13 | s9.std.RMS | $S_9$ | std | RMS |
| 14 | s9.std.power | $S_9$ | std | power |
| 15 | s9.power.mean | $S_9$ | power | mean |
| 16 | s9.power.RMS | $S_9$ | power | RMS |
| 17 | s9.power.power | $S_9$ | power | power |

In the table above of selected features:
1. in the "Segment" column, references to $S_1$, $S_4$, $S_7$, and $S_9$ are references to those segments as described above;
2. in the "Time Series" column,
   a. "mean" refers to the time series of mean amplitude of the segment as described above,
   b. "std" refers to the time series of standard deviation of amplitude of the segment as described above,
   c. "power" refers to the time series of power as described above; and
3. in the "Feature" column,
   a. "std" refers to the extracted feature of standard deviation as described above,
   b. "mean" refers to the extracted feature of mean as described above, c. "RMS" refers to the extracted feature of root mean square as described above,
d. "power" refers to the extracted feature of power as described above, and
e. "wavelet.entropy" refers to the extracted feature of wavelet entropy as described above.

In CAD detection study #2, a binary multivariate logistic regression classifier was trained by multivariate model development using the features extracted from the measurements for subjects in the training group. A least absolute shrinkage and selection operator ("LASSO") was used to select the relevant features and to develop the CAD classifier using a glmnet R package having a tuning parameter, which was adjusted through a 5-fold cross validation.

Also, in CAD detection study #2, logistic regression was used to estimate a probability that a subject had or did not have CAD. Later, the estimated probability was tested against a decision threshold (t) to classify the subject as having or not having CAD. For a given decision threshold, the performance of the CAD classifier can be summarized by a 2×2 confusion matrix shown below.

|  | Predicted non-CAD | Predicted CAD | Total |
|---|---|---|---|
| True non-CAD | TN(t) | FP(t) | $n_0$ |
| True CAD | FN(t) | TP(t) | $n_1$ |
| Total | PN(t) | PP(t) | n |

In the confusion matrix shown above:
1. TN(t) is a number of true negative subjects (in CAD detection study #2, a number of the subjects who actually do not have CAD and who are predicted by the CAD classifier not to have CAD) for a decision threshold t;
2. FP(t) is a number of false positives (in CAD detection study #2, a number of the subjects who actually do not have CAD but who are predicted by the CAD classifier to have CAD) for a decision threshold t;
3. FN(t) is a number of false negatives (in CAD detection study #2, a number of the subjects who actually have CAD but who are predicted by the CAD classifier not to have CAD) for a decision threshold t;
4. TP(t) is a number of true positive subjects (in CAD detection study #2, a number of the subjects who actually have CAD and who are predicted by the CAD classifier to have CAD) for a decision threshold t;
5. PN(t)=TN(t)+FN(t) is a total number of predicted-negative subjects (in CAD detection study #2, a number of the subjects who are predicted by the CAD classifier not to have CAD) for a decision threshold t;
6. PP(t)=FP(t)+TP(t) is a total number of predicted-positive subjects (in CAD detection study #2, a number of the subjects who are predicted by the CAD classifier to have CAD) for a decision threshold t;
7. $n_0$=TN(t)+FP(t) is an actual number of negative subjects (in CAD detection study #2, a number of the subjects who actually do not have CAD);
8. $n_1$=FN(t)+TP(t) is an actual number of positive subjects (in CAD detection study #2, a number of the subjects who actually do have CAD); and
9. n=$n_0$+$n_1$=PN(t)+PP(t) is the total number of subjects.

For each decision threshold, sensitivity may be estimated as TP(t)/$n_1$, specificity may be estimated as TN(t)/$n_0$, and accuracy may be estimated as (TP(t)+TN(t))/($n_0$+$n_1$). Therefore, sensitivity, specificity, and accuracy of the model depend on the decision threshold t. In CAD detection study #2, a decision threshold of the CAD classifier was estimated to maximize a weighted classification score defined as the number of correct identifications of CAD plus the number of correct identifications of no CAD.

Figure 28:
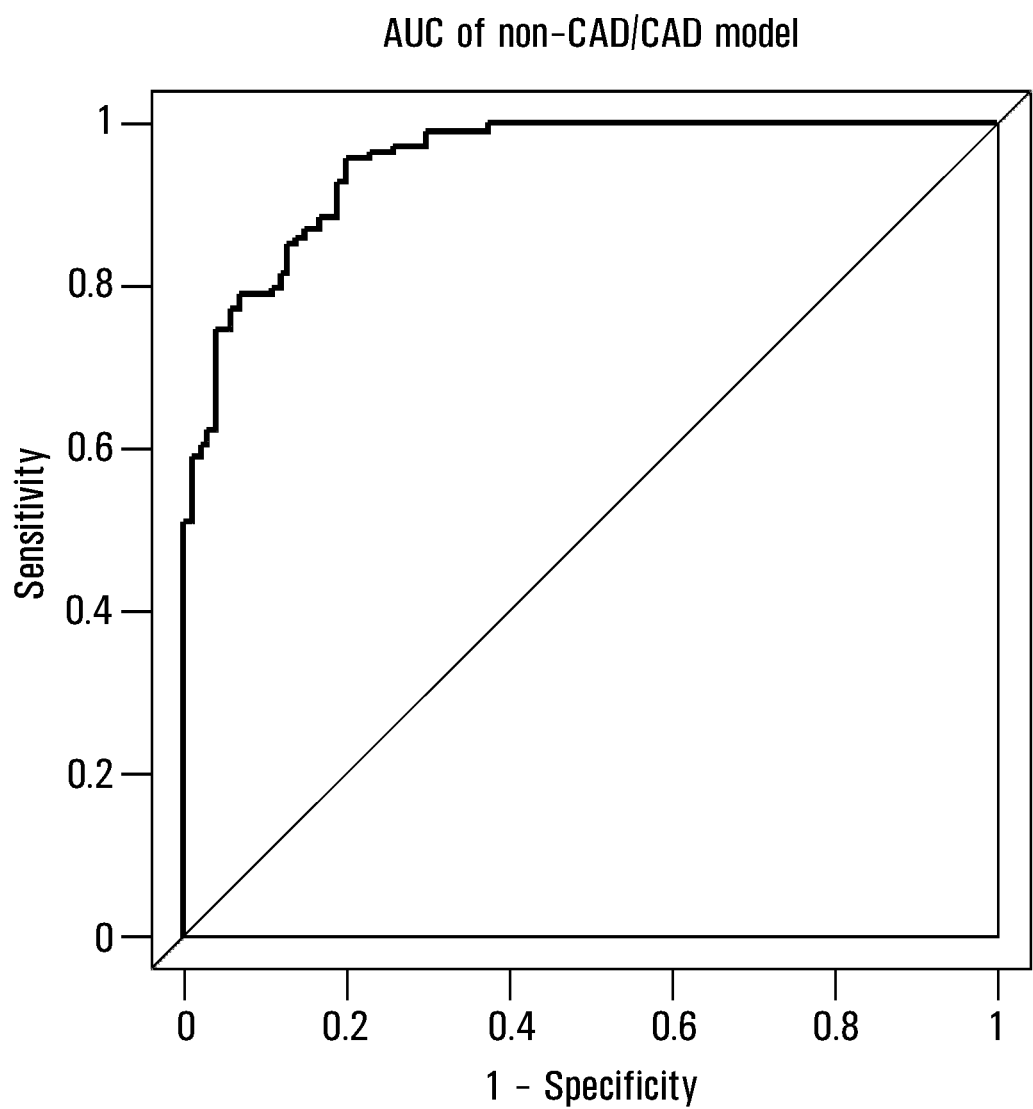
FIG. 28 illustrates a receiver operating characteristic curve of a probabilistic model trained according to the detection study of FIG. 27.

In CAD detection study #2, the measurements from the subjects in the test group were tested in the trained CAD classifier, resulting in an AUC of 0.95 with a 95% confidence interval ("CI") from 0.90 to 0.97. FIG. 28 illustrates AUC of the receiver operating characteristic ("ROC") curve of the CAD classifier. The decision threshold was estimated as t=0.57. The accuracy, sensitivity, and specificity values were estimated 83%, 85% and 81%, respectively.

As indicated above, CAD detection study #2 involved segmentation similar to segmentation shown in FIGS. 19 and 21. Further, CAD detection study #2 involved feature extraction, classification, and probability as shown in FIG. 15. Therefore, CAD detection study #2 is an example of methodology that is also illustrated in FIGS. 15, 19, and 21 and otherwise described herein, for example.

CAD detection study #2 is an example only, and other models associated with CAD or with one or more other cardiac diseases may be trained in similar ways or in different ways.

D. Summary

In general, embodiments such as those described herein may involve a combination of ECG, SCG, and GCG measurements, which may facilitate a comprehensive cardiac assessment testing procedure that may involve assessment of overall performance of cardiac function of a heart by monitoring electromechanical behavior of the heart.

Some embodiments such as those described herein may facilitate personal health monitoring. For example, embodiments such as those described herein may include one or more relatively small sensor devices that may measure measurements (such as those described herein, for example) of a heart of a subject and that may analyze such measurements and/or produce and transmit one or more signals for one or more other computing devices (such as one or more local or remote computing devices as described herein, for example) to provide one or more inferences (as described herein, for example) to the subject or to another individual such as a medical professional, for example.

Also, embodiments such as those described herein may be used by and/or with professional health care providers.

Embodiments such as those described herein may provide a more comprehensive procedure for assessment of cardiac function and for screening for cardiovascular abnormalities when compared to other technologies used for personal health monitoring or by health care providers.

Although specific embodiments have been described and illustrated, such embodiments should be considered illustrative only and not as limiting the invention as construed according to the accompanying claims.

The invention claimed is:
1. A method of analyzing electromechanical characteristics of a heart of a subject, the method comprising producing at least one inference, wherein producing the at least one inference comprises analyzing, in at least one model, each model of the at least one model associated with a respective type of inference, at least:
a time series of electrocardiogram (ECG) measurements of the heart and measured during a first period of time; and
a time series of measurements of movement caused by the heart during a second period of time at least overlapping with the first period of time, wherein the mea- surements of movement comprise measurements of rotational movement caused by the heart around at least one axis of rotation;

wherein producing the at least one inference comprises feature extraction of at least one time segment of, at least, the time series of measurements of movement; and wherein the at least one time segment comprises a low-energy diastole time segment defined as between:
- an end of diastolic vibration identified in the time series of measurements of movement; and
- an immediately subsequent "Q" wave of the time series of ECG measurements.

2. The method of claim 1 wherein at least one of the at least one model is associated with at least one cardiac disease.

3. The method of claim 2 wherein the at least one cardiac disease comprises coronary artery disease.

4. The method of claim 1 wherein the at least one time segment further comprises a first low-energy systole time segment defined as between:
- a "Q" wave of the time series of ECG measurements; and
- an immediately subsequent start of systolic vibration identified in the time series of measurements of movement.

5. The method of claim 1 wherein the at least one time segment further comprises a high-energy systole time segment defined as between:
- a start of systolic vibration identified in the time series of measurements of movement; and
- an immediately subsequent end of systolic vibration identified in the time series of measurements of movement.

6. The method of claim 1 wherein the at least one time segment further comprises a high-energy diastole time segment defined as between:
- a start of diastolic vibration identified in the time series of measurements of movement; and
- an immediately subsequent end of diastolic vibration identified in the time series of measurements of movement.

7. The method of claim 1 wherein the at least one time segment further comprises:
- a systole time segment defined as between:
  - a "Q" wave of the time series of ECG measurements; and
  - an immediately subsequent start of diastolic vibration identified in the time series of measurements of movement; and
- a diastole time segment defined as between:
  - a start of diastolic vibration identified in the time series of measurements of movement; and
  - an immediately subsequent "Q" wave of the time series of ECG measurements.

8. At least one computer-readable medium comprising codes stored thereon that, when executed by at least one processor, cause the at least one processor to implement a method of analyzing electromechanical characteristics of a heart of a subject, the method comprising producing at least one inference, wherein producing the at least one inference comprises analyzing, in at least one model, each model of the at least one model associated with a respective type of inference, at least:
- a time series of electrocardiogram (ECG) measurements of the heart and measured during a first period of time; and
- a time series of measurements of movement caused by the heart during a second period of time at least overlapping with the first period of time, wherein the measurements of movement comprise measurements of rotational movement caused by the heart around at least one axis of rotation;

wherein producing the at least one inference comprises feature extraction of at least one time segment of, at least, the time series of measurements of movement; and wherein the at least one time segment comprises a low-energy diastole time segment defined as between:
- an end of diastolic vibration identified in the time series of measurements of movement; and
- an immediately subsequent "Q" wave of the time series of ECG measurements.

9. The method of claim 1 wherein the at least one time segment further comprises:
- a first low-energy systole time segment defined as between:
  - a "Q" wave of the time series of ECG measurements; and
  - an immediately subsequent start of systolic vibration identified in the time series of measurements of movement;
- a high-energy systole time segment defined as between:
  - a start of systolic vibration identified in the time series of measurements of movement; and
  - an immediately subsequent end of systolic vibration identified in the time series of measurements of movement; and
- a high-energy diastole time segment defined as between:
  - a start of diastolic vibration identified in the time series of measurements of movement; and
  - an immediately subsequent end of diastolic vibration identified in the time series of measurements of movement.

10. The method of claim 1 wherein:
the feature extraction comprises extraction of at least one feature of morphology of the measurements of movement; and
producing the at least one inference comprises producing the at least one inference according to, at least, the at least one feature of morphology.

11. The method of claim 1 wherein:
the feature extraction comprises extraction of at least one feature of frequency of the measurements of movement; and
producing the at least one inference comprises producing the at least one inference according to, at least, the at least one feature of frequency.

12. The method of claim 1 wherein:
the feature extraction comprises extraction of at least one cross feature associated with different segments of different types of measurements of vibration; and
producing the at least one inference comprises producing the at least one inference according to, at least, the at least one cross feature.

13. The method of claim 1 wherein the at least one axis of rotation comprises two axes of rotation.

14. The method of claim 13 wherein the at least two axes of rotation comprise a lateral-medial axis of rotation relative to the subject and a superior-inferior axis of rotation relative to the subject.

15. The method of claim 1 wherein the measurements of rotational movement comprise measurements by at least one gyroscope.

16. The method of claim 1 wherein the measurements of movement further comprise measurements of linear movement caused by the heart in at least one linear direction.

17. The method of claim 16 wherein the at least one linear direction comprises a front-to-back direction relative to the subject.

18. The method of claim 16 wherein:
the at least one linear direction comprises three linear directions; and
the at least one axis of rotation comprises three axes of rotation.

19. A sensor system comprising:
a sensor apparatus comprising an electrocardiogram (ECG) sensor and at least one movement sensor;
at least one signal interface; and
at least one processor circuit configured to, at least, cause the at least one signal interface to produce at least one output signal representing at least one inference, wherein the at least one processor circuit is configured to produce the at least one inference by, at least, analyzing, in at least one model, each model of the at least one model associated with a respective type of inference, at least:
a time series of ECG measurements, by the ECG sensor, of a heart and measured during a first period of time; and
a time series of measurements, by the at least one movement sensor, of movement caused by the heart during a second period of time at least overlapping with the first period of time, wherein the measurements of movement comprise measurements of rotational movement caused by the heart around at least one axis of rotation;
wherein producing the at least one inference comprises feature extraction of at least one time segment of, at least, the time series of measurements of movement; and
wherein the at least one time segment comprises a low-energy diastole time segment defined as between:
an end of diastolic vibration identified in the time series of measurements of movement; and
an immediately subsequent "Q" wave of the time series of ECG measurements.

20. The method of claim 1 wherein analyzing in the at least one model comprises analyzing one or more peak twist/untwist velocity intervals, each defined as a time interval between a time of maximum twist velocity during systole and a time of maximum twist velocity during diastole.

21. The method of claim 1 wherein analyzing in the at least one model comprises analyzing rotational twist/untwist velocity.

22. The method of claim 1 wherein producing the at least one inference comprises producing an estimate of cardiac fitness.

23. The method of claim 1 wherein the at least one time segment further comprises a second low-energy systole time segment defined as between:
an end of systolic vibration identified in the time series of measurements of movement; and
an immediately subsequent start of diastolic vibration identified in the time series of measurements of movement.

24. The method of claim 4 wherein the at least one time segment further comprises:
a high-energy systole time segment defined as between:
a start of systolic vibration identified in the time series of measurements of movement; and
an immediately subsequent end of systolic vibration identified in the time series of measurements of movement; and
a second low-energy systole time segment defined as between:
an end of systolic vibration identified in the time series of measurements of movement; and
an immediately subsequent start of diastolic vibration identified in the time series of measurements of movement.

25. The method of claim 9 wherein the at least one time segment further comprises a second low-energy systole time segment defined as between:
an end of systolic vibration identified in the time series of measurements of movement; and
an immediately subsequent start of diastolic vibration identified in the time series of measurements of movement.

26. The method of claim 5 wherein the at least one time segment further comprises a high-energy diastole time segment defined as between:
a start of diastolic vibration identified in the time series of measurements of movement; and
an immediately subsequent end of diastolic vibration identified in the time series of measurements of movement.

* * * * *